US010620719B2

(12) United States Patent
Kaneko

(10) Patent No.: US 10,620,719 B2
(45) Date of Patent: Apr. 14, 2020

(54) INFORMATION PROCESSING DEVICE AND INFORMATION PROCESSING METHOD

(71) Applicant: SONY CORPORATION, Tokyo (JP)

(72) Inventor: Akihisa Kaneko, Tokyo (JP)

(73) Assignee: Sony Corporation, Tokyo (JP)

( * ) Notice: Subject to any disclaimer, the term of this patent is extended or adjusted under 35 U.S.C. 154(b) by 54 days.

(21) Appl. No.: 15/760,936

(22) PCT Filed: Jul. 20, 2016

(86) PCT No.: PCT/JP2016/071317
§ 371 (c)(1),
(2) Date: Mar. 16, 2018

(87) PCT Pub. No.: WO2017/056651
PCT Pub. Date: Apr. 6, 2017

(65) Prior Publication Data
US 2018/0267627 A1    Sep. 20, 2018

(30) Foreign Application Priority Data

Sep. 30, 2015   (JP) .................................. 2015-193114

(51) Int. Cl.
*G06F 3/0346* (2013.01)
*G06F 3/0488* (2013.01)
(Continued)

(52) U.S. Cl.
CPC ............ *G06F 3/0346* (2013.01); *A61B 34/25* (2016.02); *G06F 3/017* (2013.01); *G06F 3/0304* (2013.01);
(Continued)

(58) Field of Classification Search
CPC ............... G06F 3/0346; G06F 3/04842; G06F 3/04883; G06F 3/0304; G06F 3/017;
(Continued)

(56) References Cited

U.S. PATENT DOCUMENTS

2005/0235226 A1* 10/2005 Watanabe ........... G06F 3/04812
715/835
2007/0257891 A1* 11/2007 Esenther ................. G06F 3/044
345/173
(Continued)

FOREIGN PATENT DOCUMENTS

JP    2007-299384 A    11/2007
JP    2012-221498 A    11/2012
(Continued)

OTHER PUBLICATIONS

International Search Report & Written Opinion of PCT Application No. PCT/JP2016/071317, dated Aug. 16, 2016, 08 pages.

Primary Examiner — Mark W Regn
(74) Attorney, Agent, or Firm — Chip Law Group

(57) ABSTRACT

[Object] There has been a demand for a technique of improving the manipulability in a case in which an input manipulation is performed using a plurality of manipulators. [Solution] According to the present disclosure, provided is an information processing device including a control unit that performs an action based on an indication position in a display region on the basis of movement of a plurality of manipulators and restricts movement of the indication position responsive to a pointing manipulation. According to the present disclosure, it is possible to perform the action based on the indication position in the display region more accurately. Therefore, according to the present disclosure, it is possible to improve manipulability in a case in which an input manipulation is performed using a plurality of manipulators.

19 Claims, 12 Drawing Sheets

(51) Int. Cl.
- *G06F 3/0484* (2013.01)
- *G06K 9/00* (2006.01)
- *G06F 3/03* (2006.01)
- *A61B 34/00* (2016.01)
- *G06F 3/038* (2013.01)
- *G06F 3/01* (2006.01)

(52) U.S. Cl.
CPC .......... *G06F 3/038* (2013.01); *G06F 3/04842* (2013.01); *G06F 3/04883* (2013.01); *G06K 9/00355* (2013.01); *G06F 2203/04808* (2013.01)

(58) Field of Classification Search
CPC ........... G06F 3/038; G06F 2203/04808; A61B 34/25; G06K 9/00355
See application file for complete search history.

(56) References Cited

U.S. PATENT DOCUMENTS

| | | | |
|---|---|---|---|
| 2015/0062033 A1 | 3/2015 | Ishihara | |
| 2015/0242074 A1* | 8/2015 | Iwamoto | G06F 3/0483 345/158 |

FOREIGN PATENT DOCUMENTS

| | | |
|---|---|---|
| JP | 2013-228948 A | 11/2013 |
| WO | 2015/059992 A1 | 4/2015 |

\* cited by examiner

INFORMATION PROCESSING DEVICE AND INFORMATION PROCESSING METHOD

CROSS REFERENCE TO RELATED APPLICATIONS

This application is a U.S. National Phase of International Patent Application No. PCT/JP2016/071317 filed on Jul. 20, 2016, which claims priority benefit of Japanese Patent Application No. JP 2015-193114 filed in the Japan Patent Office on Sep. 30, 2015. Each of the above-referenced applications is hereby incorporated herein by reference in its entirety.

TECHNICAL FIELD

The present disclosure relates to an information processing device, an information processing method, and a program.

BACKGROUND ART

A technique of controlling an operation of an object on the basis of a gesture manipulation of a user is disclosed in Patent Literature 1.

CITATION LIST

Patent Literature

Patent Literature 1: JP 2012-221498A

DISCLOSURE OF INVENTION

Technical Problem

Meanwhile, in recent years, in a case in which an input manipulation is performed using a plurality of manipulators, there is a demand for further improvement in manipulability, but the technique disclosed in Patent Literature 1 is unable to sufficiently meet such a demand.

For this reason, there has been a demand for a technique of improving the manipulability in a case in which an input manipulation is performed using a plurality of manipulators.

Solution to Problem

According to the present disclosure, there is provided an information processing device including a control unit configured to decide an indication position for specifying a position in a display region on a basis of positions of a plurality of manipulators. The control unit restricts movement of the indication position responsive to movement of the manipulator on a basis of a state of the manipulator.

According to the present disclosure, there is provided an information processing method including deciding, by a control unit, an indication position for specifying a position in a display region on a basis of positions of a plurality of manipulators, and restricting movement of the indication position responsive to movement of the manipulator on a basis of a state of the manipulator.

According to the present disclosure, there is provided a program causing a computer to execute a control function of deciding an indication position for specifying a position in a display region on a basis of positions of a plurality of manipulators. The control function restricts movement of the indication position responsive to movement of the manipulator on a basis of a state of the manipulator.

According to the present disclosure, since movement of an indication position responsive to movement of a manipulator is restricted on the basis of a state of the manipulator, it is possible to perform an action based on an indication position in a display region more accurately.

Advantageous Effects of Invention

As described above, according to the present disclosure, it is possible to perform an action based on an indication position in a display region more accurately. Therefore, according to the present disclosure, it is possible to improve the manipulability in a case in which an input manipulation is performed using a plurality of manipulators. Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
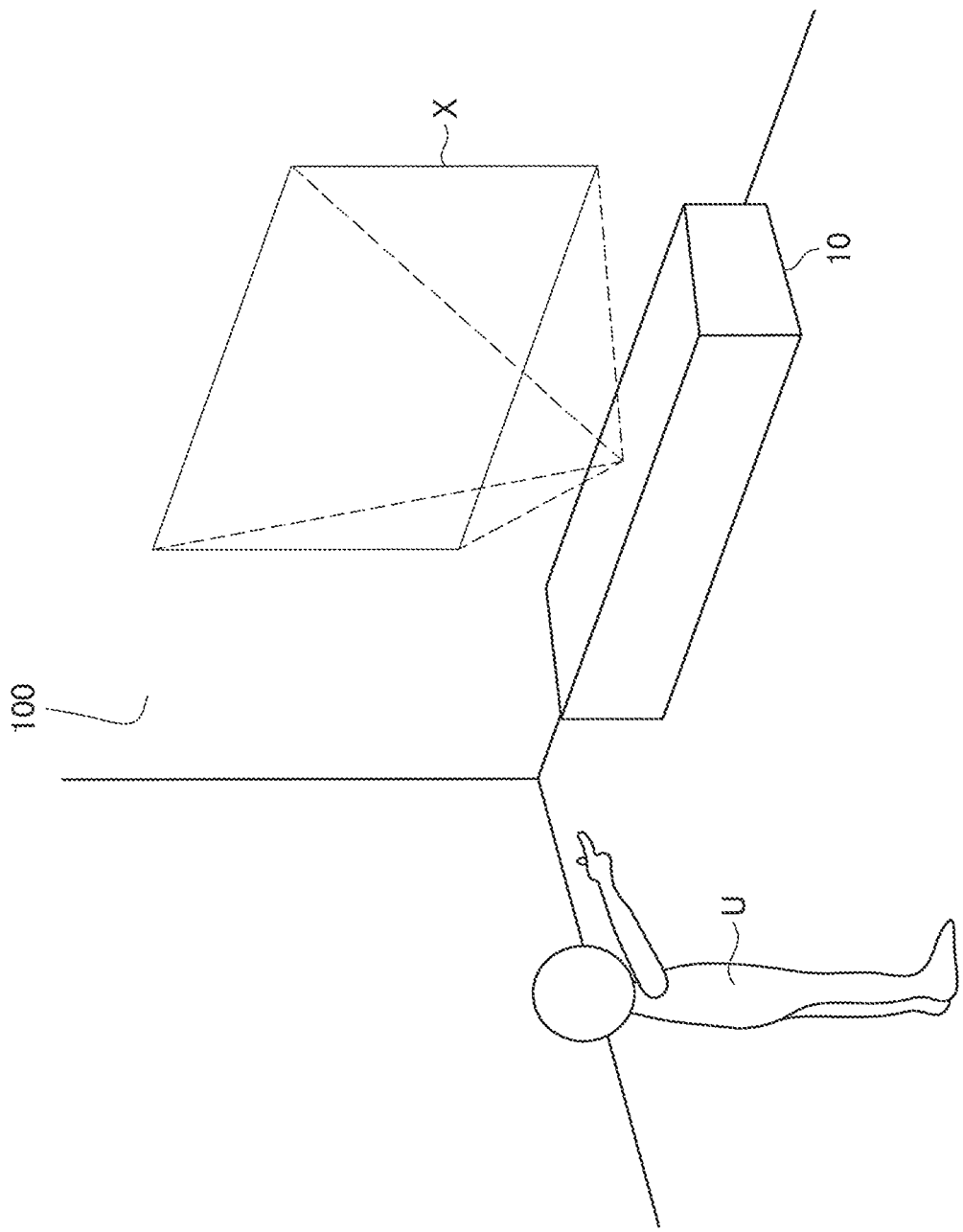
FIG. 1 is a perspective view illustrating an application example of an information processing device according to the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Further, the description will proceed in the following order.
1. Overview of present embodiment
2. Configuration of information processing device
3. Basic process performed by information processing device
4. First modified example
5. Second modified example
6. Third modified example
7. Fourth modified example
8. Fifth modified example
9. Sixth modified example
10. Seventh modified example
11. Eighth modified example
12. Ninth modified example
13. Tenth modified example
14. Eleventh modified example
15. Twelfth modified example
16. Thirteenth modified example
17. Field of application

1. Overview of Present Embodiment

First, an overview of the present embodiment will be described with reference to FIG. 1. In the present embodiment, a person U (that is, a user) performs a gesture manipulation as illustrated in FIG. 1. Here, examples of the gesture manipulation performed by the user include a pointing manipulation, a pinch-in manipulation, and a pinch-out manipulation. Specifically, the user points a hand having a pinch-in manipulation attitude forward. Then, the user moves the hand forward in a state in which the pinch-in manipulation attitude is maintained. Accordingly, the user performs the pointing manipulation. Here, the pinch-in manipulation attitude indicates an attitude in which a plurality of fingers of the same hand are widened. Examples of a combination of a plurality of fingers include a combination of an index finger (a second manipulator), a middle finger (second manipulator), and a thumb (a first manipulator), a combination of the index finger and the thumb, and the like. The user may take the pinch-in manipulation attitude using four to five fingers. The pinch-in manipulation is a manipulation of narrowing an interval between widened fingers. In other words, the pinch-in manipulation is a manipulation of pinching an object. The pinch-out manipulation is a reverse manipulation of the pinch-in manipulation, that is, a manipulation of widening an interval between narrowed fingers (that is, performing the pinch-in manipulation attitude again).

On the other hand, an information processing device 10 displays various kinds of objects in a display region X. Here, the object displayed in the display region X is not particularly limited. In other words, the object may be any image. Examples of the object include various kinds of texts (including text boxes or the like), pictures (including photographs, illustrations, or the like), buttons (including radio buttons or the like), seek bars, check boxes, draggable images, electronic books (including parts for turning over pages of electronic books), and the like.

Further, the information processing device 10 detects positions of a plurality of fingers and specifies a display position of a fingertip image for each of a plurality of fingers in the display region X on the basis of the positions. Further, the information processing device 10 decides a center of gravity position of the display positions as an indication position. Here, the indication position specifies a position in the display region. Specifically, the information processing device 10 recognizes the indication position as a position indicated by the user. Then, the information processing device 10 causes a cursor to be displayed at the indication position and causes the fingertip image to be displayed at the display position (see FIG. 4 or the like). Therefore, the user can cause the cursor to be moved to a desired position by performing the pointing manipulation. Further, the fingertip image may not be displayed. Particularly, the fingertip image may not be displayed in a region in which objects are densely placed.

Further, if the user performs the pinch-in manipulation, a distance between the display positions is narrowed. Further, the information processing device 10 fixes the indication position in a case in which the distance (a determination distance to be described later) is less than a predetermined restriction start threshold value. Further, in a case in which the determination distance is less than a predetermined action start threshold value, the information processing device 10 selects an object placed on the indication position. Therefore, the user can fix the indication position or select a desired object by performing the pinch-in manipulation. In other words, the user performs an object selection manipulation (that is, a decision manipulation) by performing the pinch-in manipulation. Further, the information processing device 10 cancels the fixing of the indication position in a case in which the user performs the pinch-out manipulation.

As described above, in the present embodiment, the information processing device 10 performs a process according to the gesture manipulation of the user. Here, since the gesture manipulation is performed in a space, there is mostly little physical feedback on the gesture manipulation. Here, the physical feedback indicates, for example, a stimulus to a tactile sensation of the user. For example, in a case in which the user touches a touch panel, the fingertip of the user has a feeling of touching the touch panel. Therefore, the physical feedback is given. However, since the gesture manipulation is performed in the space, there is mostly little physical feedback. Therefore, the user may feel that it is difficult to perform the object selection manipulation. For example, in a case in which the user performs the selection manipulation, it is difficult for the user to know a position in the space which the user has to touch. Further, since there is no physical feedback, it is hard for the user to determine whether or not the selection manipulation is performed properly.

Therefore, in the present embodiment, the user performs the object selection manipulation by performing the pinch-in manipulation. In a case in which the user performs the pinch-in manipulation, since the fingertips come into contact with each other, the physical feedback can be given. Therefore, the user can easily determine whether or not the object selection manipulation is performed properly.

Here, since the indication position is the center of gravity position of the display positions as described above, the indication position may be shifted during the pinch-in manipulation. One of the reasons is, for example, that a finger moving speed differs in accordance with each finger at the time of the pinch-in manipulation. For example, at the start of the pinch-in manipulation, the moving speed of the index finger mostly coincides with the moving speed of the thumb. However, as the pinch-in manipulation progresses, the moving speed of the index finger is mostly faster than the moving speed of the thumb. In this case, an object different from an object intended by the user is likely to be selected. In this regard, in the present embodiment, the indication position is fixed during the pinch-in manipulation. Accordingly, it is easier for the user to select a desired object in the present embodiment. In other words, in the present embodiment, it is possible to improve the manipulability in a case in which an input manipulation (here, the gesture manipulation) is performed using a plurality of fingers. Hereinafter, the present embodiment will be described in detail.

2. Configuration of Information Processing Device

Figure 2:
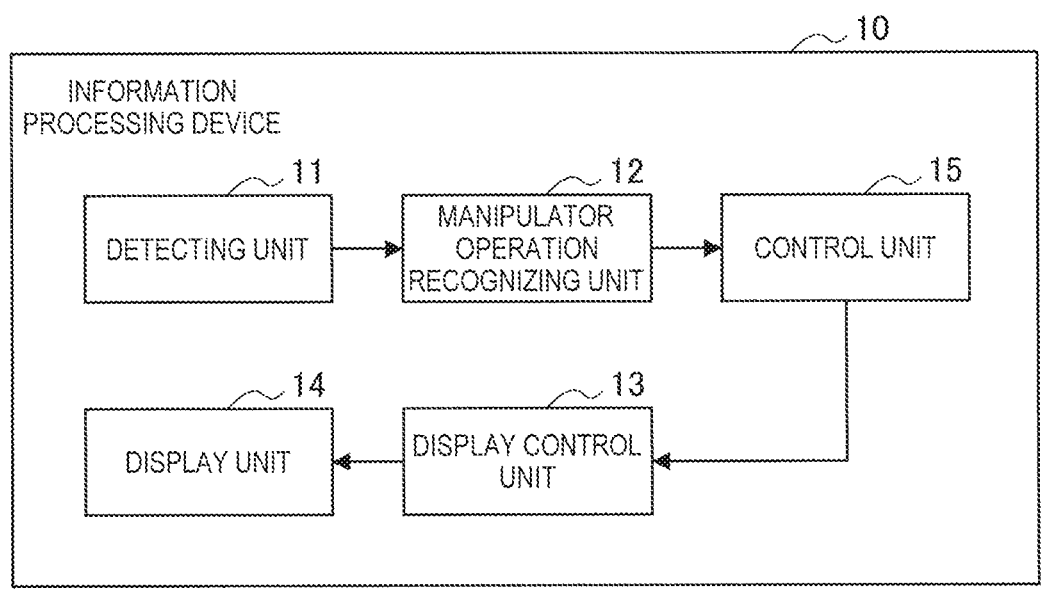
FIG. 2 is a block diagram of an information processing device according to the embodiment.

Next, an example of a configuration of the information processing device 10 according to the present embodiment will be described with reference to FIGS. 1 and 2. The information processing device 10 includes a detecting unit 11, a manipulator operation recognizing unit 12, a display control unit 13, a display unit 14, and a control unit 15. The detecting unit 11 detects the gesture manipulation of the user and outputs detection information related to the result to the manipulator operation recognizing unit 12. Here, examples of the gesture manipulation performed by the user include the pointing manipulation, the pinch-in manipulation, the pinch-out manipulation, and the like as described above. It will be appreciated that the detecting unit 11 may detect other types of gesture manipulations such as a double tap manipulation, a long press manipulation, and a drag and drop manipulation. The double tap manipulation is, for example, a manipulation of performing the pinch-in manipulation twice quickly. The long press manipulation is, for example, a manipulation of maintaining a pinch-in state (that is, a state in which the fingertips are brought into contact with each other). The long press manipulation may be distinguished in accordance with the number of fingers used for the pinch-in manipulation. For example, the drag and drop manipulation is a manipulation of moving the hands while maintaining the pinch-in state and then performing the pinch-out manipulation. A process of the present embodiment may be applied even in these manipulations. Here, the fingertips are an example of a plurality of manipulators. The detecting unit 11 is, for example, an imaging element, a depth sensor, or the like, but any device may be used as long as it can detect the gesture manipulation of the user.

The manipulator operation recognizing unit 12 recognizes the gesture manipulation of the user on the basis of the detection information. Specifically, for example, the manipulator operation recognizing unit 12 recognizes the position of the fingertip (that is, position coordinates in the space in which the user exists). Here, the manipulator operation recognizing unit 12 may recognize an absolute position of the fingertip or may recognize a relative position. Then, the manipulator operation recognizing unit 12 outputs recognition information related to a recognition result to the control unit 15.

The display control unit 13 causes the display unit 14 to display various kinds of images (for example, various kinds of objects, cursors, fingertip images, or the like) under control of the control unit 15. The display unit 14 is a so-called projector and displays various kinds of images on a wall surface 100 illustrated in FIG. 1. Here, the display unit 14 displays various kinds of images in the display region X. In the present embodiment, since the display unit 14 displays various kind of images on the wall surface 100, the display region X may have a certain size. It will be appreciated that the size of the display region X is arbitrary. Further, the display unit 14 may be of any type as long as it can display various kinds of images. For example, the display unit 14 may be a display panel or the like. Here, a type of display panel is not particularly limited, and for example, a liquid crystal display panel, an organic EL display panel, or the like may be used.

In addition to controlling an internal configuration of the information processing device 1, the control unit 15 performs, for example, the following process. In other words, the control unit 15 specifies the display positions of a plurality of fingertips in the display region X on the basis of the recognition information. For example, the control unit 15 sets a crossing point of an extension line of the finger in a length direction and the display region X as the display position. Then, the control unit 15 specifies the indication position on the basis of the display positions of a plurality of fingertips (that is, the positions of a plurality of fingertips). Specifically, the control unit 15 decides the center of gravity position of the respective display positions as the indication position. It will be appreciated that an indication position calculation method is not limited to this example. Other examples will be described later. The indication position changes as the user performs the pointing manipulation.

Further, the control unit 15 determines whether or not a predetermined restriction start condition is satisfied. Here, the restriction start condition is, for example, a condition that a predetermined determination distance is less than a predetermined restriction start threshold value. The determination distance is calculated, for example, on the basis of the position of each fingertip. If the user performs the pinch-in manipulation, the determination distance decreases, and if the user performs the pinch-out manipulation, the determination distance increases. Therefore, if the user narrows the interval between the fingertips by the pinch-in manipulation, the determination distance becomes less than the restriction start threshold value at a certain timing. It will be appreciated that the restriction start condition may be other conditions. In a case in which the restriction start condition is satisfied, the control unit 15 restricts the movement of the indication position. In other words, the control unit 15 restricts the movement of the indication position responsive to the movement of the fingertip on the basis of a state of the fingertip (for example, a relation between the determination distance and the restriction start threshold value). For example, the control unit 15 fixes the indication position. Further, the method of restricting the movement of the indication position is not limited to this example. The details will be described later.

Further, the control unit 15 restricts the movement of the indication position and then determines whether or not a predetermined restriction release condition is satisfied. Here, the restriction release condition is, for example, a condition that the above-described determination distance is larger than a predetermined restriction release threshold value. If the user increases the interval between the fingertips by the pinch-out manipulation, the determination distance becomes larger than the restriction release start threshold value at a certain timing. It will be appreciated that restriction release condition may be other condition. In a case in which the restriction release condition is satisfied, the control unit 15 cancels the restriction of the movement of the indication position.

Further, the control unit 15 restricts the movement of the indication position and then determines whether or not a predetermined action start condition is satisfied. Here, the action start condition is, for example, a condition that the above-described determination distance is less than a predetermined action start threshold value. Therefore, if the user narrows the interval between the fingertips by the pinch-in manipulation, the determination distance becomes less than the action start threshold value at a certain timing. It will be appreciated that the action start condition may be other conditions. In a case in which the action start condition is satisfied, the control unit 15 performs an action based on the indication position. For example, the control unit 15 selects an object placed on the indication position. Further, selection of an object is an example of the action based on the indication position. It will be appreciated that the action based on the indication position is not limited to this example, any action based on the indication position (that is, an action associated with the indication position) may be used. For example, the action based on the indication position may be, for example, an action of displaying a certain object or the like at the indication position. Examples of the object include a context menu related to an object on the indication position, and the like. In the context menu, for example, a list of manipulations available for objects on the indication position is displayed.

The control unit 15 outputs display control information related to the indication position, the display positions of a plurality of fingertips, an object to be displayed in the display region X, the display position of the object to the display control unit 13, and the like. The display control unit 13 causes the display unit 14 to display various kinds of images on the basis of the display control information. Specifically, the display unit 14 displays the cursor at the indication position, displays the fingertip images at the display positions of a plurality of fingertips, and displays various kinds of objects at the display position of the object. Here, the cursor is an example of a cursor, and the fingertip image is an example of a manipulator image.

Further, the information processing device 10 has a hardware configuration such as a CPU, a ROM, a RAM, a hard disk, an imaging element (or a depth sensor or the like), and a projector (or a display panel or the like). Further, the functions of the information processing device 10, that is, the detecting unit 11, the manipulator operation recognizing unit 12, the display control unit 13, the display unit 14, and the control unit 15 are implemented by with the hardware configuration. Specifically, a program for implementing the detecting unit 11, manipulator operation recognizing unit 12, the display control unit 13, the display unit 14, and the control unit 15 in the information processing device 10 is recorded in the ROM. The CPU reads the program from the ROM and executes the program. The whole or part of the program may be stored in the hard disk. The RAM is a working area of the CPU. Therefore, the CPU is substantially a main operation entity of the information processing device 10.

3. Basic Process Performed by Information Processing Device

Figure 3:
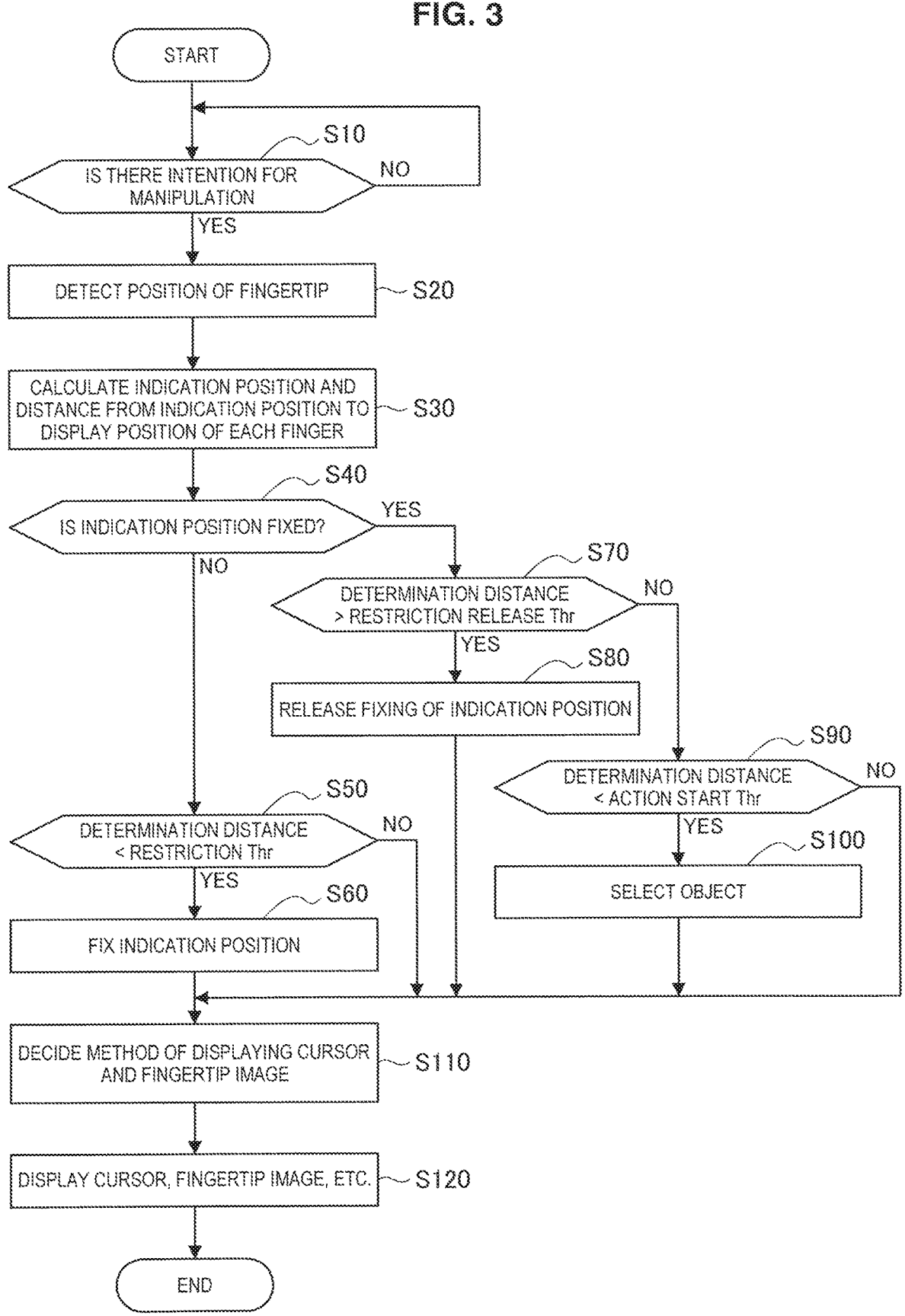
FIG. 3 is a flowchart illustrating an example of a basic process performed by an information processing device.

Next, a basic process performed by the information processing device 10 will be described with reference to a flowchart illustrated in FIG. 3. In the basic process, the user performs the pinch-in manipulation or the pinch-out manipulation using three or two fingers as the gesture manipulation using a plurality of fingertips. Then, in a case in which the user brings the fingertips close to each other by the pinch-in manipulation, the information processing device 10 fixes the indication position. In a case in which the user further performs the pinch-in manipulation, the information processing device 10 performs the action based on the indication position. On the other hand, in a case in which the user performs the pinch-out manipulation after the indication position is fixed, the information processing device 10 cancels the fixing of the indication position.

Specifically, firstly, in step S10, the control unit 15 stands by until the user shows an intention of the pointing manipulation. On the other hand, the detecting unit 11 detects the gesture manipulation of the user and outputs the detection information related to the result to the manipulator operation recognizing unit 12. The manipulator operation recognizing unit 12 determines whether or not the user points the hand forward on the basis of the detection information. Then, in a case in which the user is determined to point the hand forward, the manipulator operation recognizing unit 12 outputs the determination information indicating that the user points his hand forward to the control unit 15. In a case in which the determination information is provided, the control unit 15 determines that the user shows the intention of the pointing manipulation and causes the process to proceed to step S20. As described above, in the present embodiment, the user is determined to show the intention of the pointing manipulation in a case in which the user points the arm forward, but it will be appreciated that a determination criterion is not limited to this example. For example, a specific gesture manipulation may be registered in advance, and the user may be determined to show the intention of the pointing manipulation in a case in which the gesture manipulation is performed.

In step S20, the manipulator operation recognizing unit 12 recognizes the position of the fingertip on the basis of the detection information. Then, the manipulator operation recognizing unit 12 outputs the recognition information related to the recognition result to the control unit 15.

Figure 4:
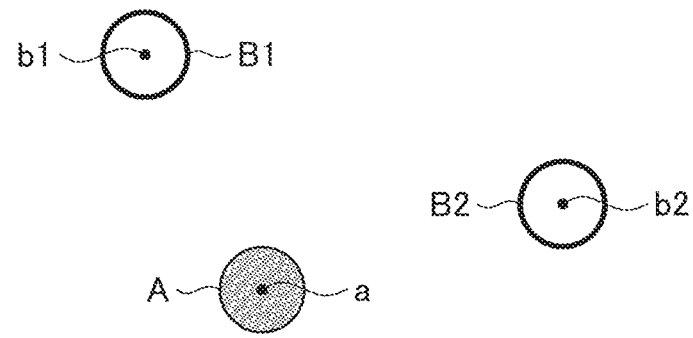
FIG. 4 is an explanatory diagram illustrating a display example performed by an information processing device.
Figure 4:
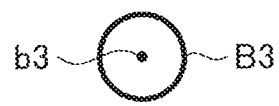
Figure 5:
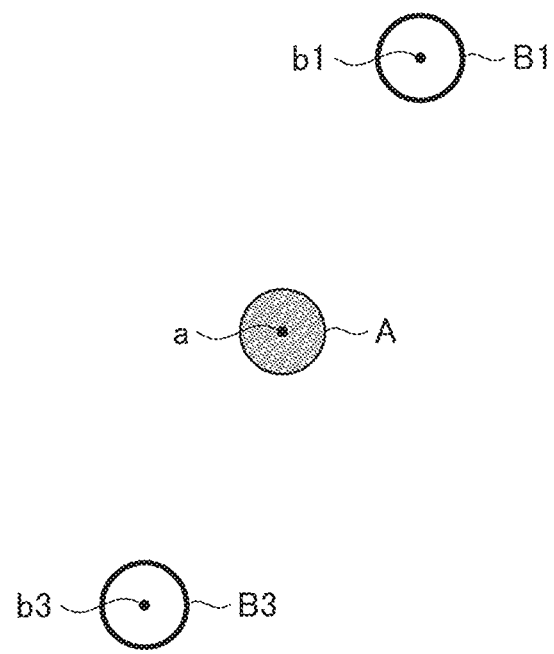
FIG. 5 is an explanatory diagram illustrating a display example performed by an information processing device.

In step S30, the control unit 15 specifies the display positions of a plurality of fingertips in the display region X on the basis of the recognition information. Then, the control unit 15 specifies the indication position on the basis of the display positions of a plurality of fingertips. Specifically, the control unit 15 decides the center of gravity position of the respective display positions as the indication position. As will be described later, the cursor is displayed at the indication position, and the fingertip image is displayed at the display position. The display examples are illustrated in FIGS. 4 and 5. Further, in the display examples, movement of the cursor is not restricted.

In the display example illustrated in FIG. 4, the user performs the pointing manipulation using three fingers, that is, the index finger, the middle finger, and the thumb. Then, as illustrated in FIG. 4, a cursor A and fingertip images B1 to B3 are displayed in the display region X. The fingertip image B1 is an example of the fingertip image indicating the index finger, the fingertip image B2 is an example of the fingertip image indicating the middle finger, and the fingertip image B3 is an example of the fingertip image indicating the thumb. Further, the fingertip image B1 is displayed at a display position b1, the fingertip image B2 is displayed at a display position b2, and the fingertip image B3 is displayed at a display position b3. Further, the cursor A is an example of a cursor and displayed at an indication position a. The indication position a is the center of gravity position of the display positions b1 to b3. All of the fingertip images B1 to B3 and the cursor A are circular images, but images of other shapes may be used. The same applies to all display examples to be described below.

In the display example illustrated in FIG. 5, the user performs the pointing manipulation using two fingers, that is, the index finger and the thumb. Then, as illustrated in FIG. 5, the cursor A and the fingertip images B1 and B3 are displayed in the display region X. The fingertip image B1 is displayed at the display position b1, and the fingertip image B3 is displayed at the display position b3. Further, the cursor A is displayed at the indication position a. The indication position a becomes the center of gravity position of the display positions b1 and b3, that is, a center position of a line segment passing through the display positions b1 and b3.

As described above, the indication position is specified on the basis of the display positions of a plurality of fingertip images. Therefore, the user can move the indication position, that is, the cursor to a desired position by performing the pointing manipulation. Therefore, in the present embodiment, the manipulation of moving the indication position, that is, the pointing manipulation is performed using a plurality of fingertips. Further, an example of performing the pointing manipulation using a plurality of manipulators other than fingertips will be described later.

Further, it will be appreciated that the indication position may be set to a position other than the center of gravity position of the display positions. For example, the indication position may be shifted from the center of gravity position by weighting the respective display positions. For example, the indication position may be brought close to the display position b1 (or superimposed on the display position b1) by increasing a weight of any of the fingertip images (for example, the fingertip image B1). A type of weighting and a display position at which weighting is performed are not particularly limited and may be set in accordance with the preference of the user (for example, a strong tendency to specify an object with the index finger or the like) or the like.

Further, the control unit 15 calculates the determination distance. The determination distance is a parameter used for determining whether or not the indication position is fixed, for example. The determination distance is calculated, for example, on the basis of the position of each fingertip. More specifically, the determination distance is calculated on the basis of the display position and/or the indication position specified on the basis of the position of the fingertip. For example, the determination distance may be a distance from any one display position (for example, the display position b1 illustrated in FIG. 4) to the indication position. The display position used for the calculation of the determination distance may be selected by the user or may be selected in advance. Further, the determination distance may be a distance from the display position closest to the indication position to the indication position. Further, the determination distance may be an arithmetic mean value of the distances from the respective display positions to the indication position. Further, the determination distance may be a distance between the positions of the respective fingertips recognized by the manipulator operation recognizing unit 12. In other words, the control unit 15 may calculate the determination distance on the basis of the positions of the respective fingertips. Among the values, the control unit 15 may use a preselected value, a value selected by the user, or a value differing for each basic process. If the user performs the pinch-in manipulation, the interval between the fingertips is narrowed. In other words, the determination distance decreases. Therefore, if the user performs the pinch-in manipulation, the determination distance becomes less than the restriction start threshold value at a certain timing.

In step S40, the control unit 15 determines whether or not the indication position is fixed. In a case in which the indication position is determined to be fixed, the control unit 15 causes the process to proceed to step S70, and in a case in which the indication position is determined not to be fixed, the control unit 15 causes the process to proceed to step S50.

In step S50, the control unit 15 determines whether or not the restriction start condition is satisfied. Specifically, the control unit 15 determines whether or not the determination distance is less than a predetermined restriction start threshold value. In a case in which the determination distance is determined to be less than the restriction start threshold value (Thr for starting restriction), the control unit 15 causes the process to proceed to step S60, and in a case in which the determination distance is determined to be equal to or larger than the restriction start threshold value, the control unit 15 causes the process to proceed to step S110.

Figure 6:
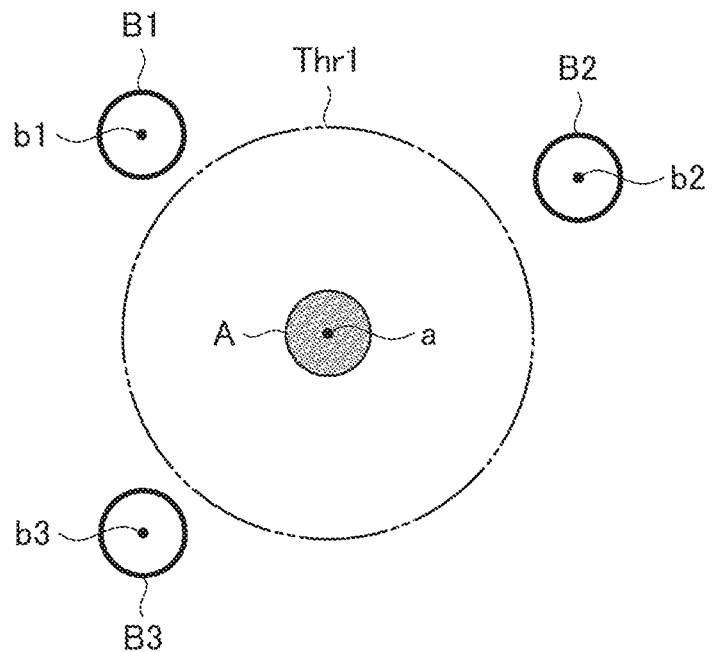
FIG. 6 is an explanatory diagram illustrating a display example performed by an information processing device.
Figure 7:
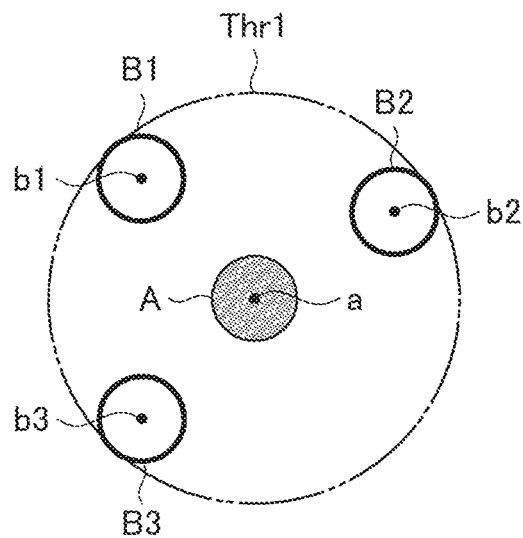
FIG. 7 is an explanatory diagram illustrating a display example performed by an information processing device.

FIG. 6 illustrates an example in which the determination distance is equal to or larger than the restriction start threshold value, and FIG. 7 illustrates an example in which the determination distance is less than the restriction start threshold value. A frames Thr1 in FIGS. 6 and 7 indicate the restriction start threshold value. In other words, a center point of the frame Thr1 is the indication position a, and the radius is the restriction start threshold value. In FIG. 6, all of the display positions b1 to b3 of the fingertip images B1 to B3 are arranged outside the frame Thr1. Therefore, the determination distance is equal to or larger than the restriction start threshold value. On the other hand, in FIG. 7, all of the display positions b1 to b3 of the fingertip images B1 to B3 are arranged inside the frame Thr1. Therefore, the determination distance is less than the restriction start threshold value. Further, the frame Thr1 is not displayed but may be displayed. The same applies to other frames Thr 2, Thr 3 to be described later.

Further, the restriction start threshold value may be a fixed value or a variable value. In a case in which the restriction start threshold value is a variable value, control unit 15 may set the restriction start threshold value on the basis of various information. For example, the control unit 15 may set the restriction start threshold value on the basis of a feature of the user. Here, examples of the feature of the user include a size of the hand, a size of the body, a classification of an adult and a kid, and an angle between the fingers.

The control unit 15 may increase the restriction start threshold value as the size of the hand increases. It is because the distance between the fingertips at the start of the pinch-in manipulation is estimated to increase as the size of the hand increases. Here, the size of the hand can be specified on the basis of the detection information.

The control unit 15 may increase the restriction start threshold value as the size of the body increases. It is because the distance between the fingertips at the start of the pinch-in manipulation is estimated to increase as the size of the body increases. Here, the size of the body can be specified on the basis of the detection information.

Further, the control unit 15 may set the restriction start threshold value in a case in which the user is an adult to be larger than the restriction start threshold value in a case in which the user is a kid. It is because in a case in which the user is an adult, the distance between the fingertips at the start of the pinch-in manipulation is estimated to increase. Thus, for example, in a case in which the user is a kid, the determination distance at the start of the pinch-in manipulation is unlikely to be a value less than the restriction start threshold value. Further, in a case in which the user is an adult, it is difficult for the restriction start threshold value is unlikely to be much smaller than the determination distance at the start of the pinch-in manipulation (that is, the indication position is not fixed easily). The classification of an adult and a kid may be registered in the information processing device 10 in advance or may be determined on the basis of the detection information.

Further, the control unit 15 may increase the restriction start threshold value as the angle between the fingers (for example, the angle between the index finger and the thumb city) increases. This is because the distance between the fingertips at the start of the pinch-in manipulation is estimated to increase as the angle between the fingers increases. Accordingly, the determination distance at the start of the pinch-in manipulation is unlikely to be a value less than the restriction start threshold value. The angle between the fingers can be specified on the basis of the detection information.

Further, the control unit 15 may set the restriction start threshold value on the basis of the distance from the user to the information processing device 10 (more specifically, the detecting unit 11). For example, the control unit 15 may decrease the restriction start threshold value as the distance increases. It is because the distance between the fingertips at the start of the pinch-in manipulation is estimated to decrease as the distance increases. Accordingly, the determination distance at the start of the pinch-in manipulation is unlikely to be a value less than the restriction start threshold value. The distance can be specified on the basis of the detection information.

Further, the control unit 15 may set the restriction start threshold value on the basis of a speed of the pinch-in manipulation (a fingertip moving speed at the time of the pinch-in manipulation). For example, the control unit 15 may increase the restriction start threshold value as the pinch-in manipulation speed increases. It is because, in this case, the user is estimated to have a strong intention of selecting the object on the indication position. Therefore, the user is likely to desire to fix the indication position early. The speed of the pinch-in manipulation can be measured on the basis of detection information.

Further, the control unit 15 may set the restriction start threshold value on the basis of a feature of an object on the indication position. Here, examples of the feature of the object include a size, a position, a degree of importance, the presence or absence of an operation, and an interval between objects (that is, a density). For example, the control unit 15 may increase the restriction start threshold value as the object on the indication position is larger. This is because the determination distance at the start of the pinch-in manipulation is estimated to increase as the object on the indication position is larger. For example, a region decided in accordance with the restriction start threshold value (for example, the region in the frame Thr1 illustrated in FIG. 6) may be larger than the object. Accordingly, a possibility that the user will have an uncomfortable feeling about the gesture manipulation is reduced.

Further, the control unit 15 may increase the restriction start threshold value as the object on the indication position is closer to the outer edge of the display region X. It is because the gesture manipulation of selecting the object close to the outer edge of the display region X is sometimes troublesome. Accordingly, a possibility that the user will have an uncomfortable feeling about the gesture manipulation is reduced.

Further, the control unit 15 may increase the restriction start threshold value as the importance of the object on the indication position increases. It is because a more accurate selection manipulation is estimated to be required as the importance of the object increases. Further, a determination criterion for determining the importance is not particularly limited, but for example, the user may determine the importance of each object. For example, an object involving money such as a payment button or the like may be an object with a high importance.

Further, the control unit 15 may set the restriction start threshold value in a case in which an object is moving to be larger than the restriction start threshold value in a case in which an object is stationary. This is because it is sometimes difficult for the user to select an object in a case in which an object is moving. Further, in this case, the control unit 15 may fix the indication position or may cause the indication position to follow the object. In other words, the control unit 15 may cause the indication position to be absorbed into the object. In this case, the user can select the object with a high degree of certainty. Further, an example of causing the indication position to be absorbed into the object will be described in detail in modified examples to be described later.

Further, the control unit 15 may increase the restriction start threshold value as an interval between objects decreases. It is because, in this case, there is a high possibility that an object not intended by the user will be selected. Accordingly, the user can perform a more accurate selection manipulation.

Further, the control unit 15 may set the restriction start threshold value using a combination of the above elements. For example, the control unit 15 may set the restriction start threshold value on the basis of the distance from the user to the information processing device 10 and the size of the object. Further, in addition to this, the control unit 15 may further set the restriction start threshold value on the basis of the speed of the pinch-in manipulation.

In step S60, the control unit 15 fixes the indication position. Accordingly, the control unit 15 restricts the movement of the indication position. Therefore, the control unit 15 restricts the movement of the indication position on the basis of the determination that a distance between the first manipulator and the second manipulator included in a plurality of manipulators (here, fingertips) is smaller than a first distance. Here, the first distance is a distance corresponding to the above-described restriction start threshold value. For example, the control unit 15 restricts the movement of the indication position as compared with a state in which the movement of the indication position is not restricted. Further, the method of restricting the movement of the indication position is not limited to this example. For example, a gain of a variation amount of the indication position with respect to a variation amount of the display position may be reduced. Specifically, for example, the control unit 15 specifies the indication position through a similar process as in step S30. Then, the control unit 15 calculates the variation amount and a variation direction of the indication position on the basis of a previous indication position and a current indication position. Then, the control unit 15 corrects the variation amount by multiplying the variation amount by a coefficient less than 1. Then, the control unit 15 moves the indication position by a corrected variation amount in the variation direction. Accordingly, the control unit 15 restricts the movement of the indication position. Thereafter, the control unit 15 causes the process to proceed to step S110. Further, the control unit 15 may restrict the movement of the cursor (that is, the image indicating the indication position) in addition to the restriction of the indication position or instead of the restriction of the indication position. A restriction method is not particularly limited and may be a restriction similar to the above-described method (for example, the position of the cursor is fixed, a gain of a variation amount of the cursor decreases, or the like).

In step S70, the control unit 15 determines whether or not the restriction release condition is satisfied. Specifically, the control unit 15 determines whether or not the determination distance is larger than a predetermined restriction release (Thr for releasing the restriction) threshold value. In a case in which the determination distance is determined to be larger than the restriction release threshold value, the control unit 15 causes the process to proceed to step S80, and in a case in which the determination distance is determined to be less than the restriction release threshold value, the control unit 15 causes the process to proceed to step S90. If the user performs the pinch-out manipulation, the interval between the fingertips increases. In other words, the determination distance increases. Therefore, if the user performs the pinch-out manipulation, the determination distance becomes larger than the restriction start threshold value at a certain timing.

Figure 8:
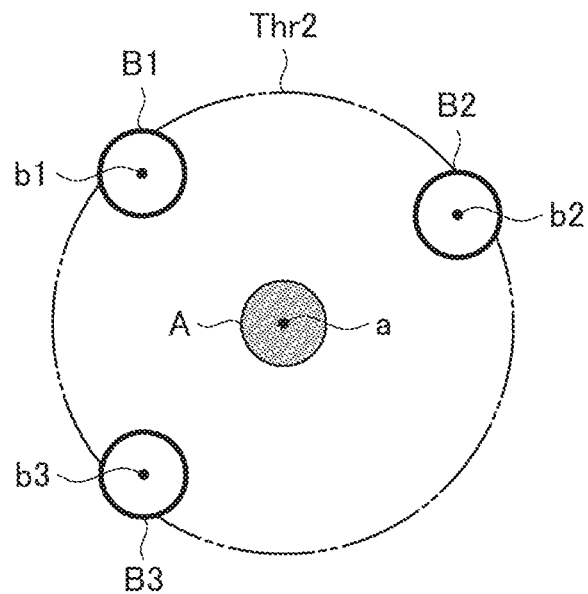
FIG. 8 is an explanatory diagram illustrating a display example performed by an information processing device.
Figure 9:
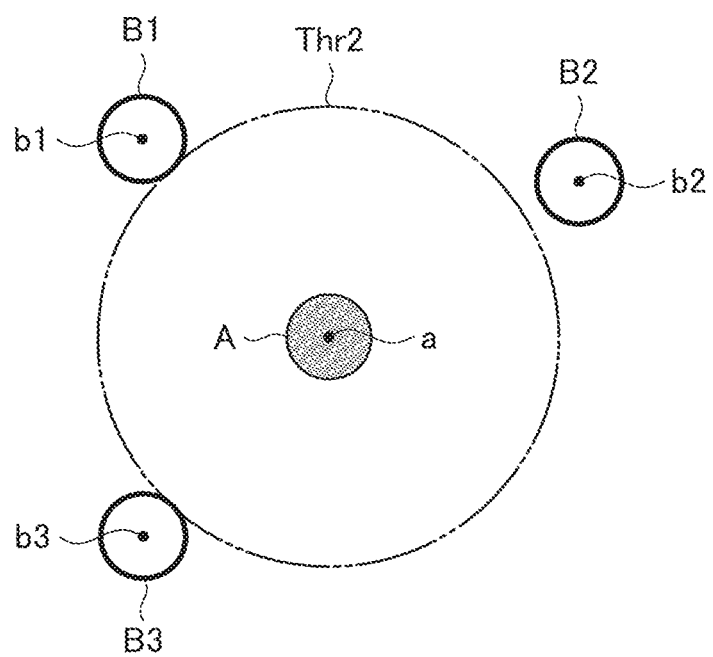
FIG. 9 is an explanatory diagram illustrating a display example performed by an information processing device.

FIG. 8 illustrates an example in which the determination distance is less than the restriction release threshold value, and FIG. 9 illustrates an example in which the determination distance is larger than the restriction release threshold value. A frame Thr2 in FIGS. 8 and 9 illustrates the restriction release threshold value. In other words, a center point of the frame Thr2 is the indication position a, and a radius is the restriction release threshold value. In FIG. 8, all of display positions b1 to b3 of fingertip images B1 to B3 are arranged inside the frame Thr2. Therefore, the determination distance is less than the restriction release threshold value. On the other hand, in FIG. 9, all of the display positions b1 to b3 of the fingertip images B1 to B3 are arranged outside the frame Thr2. Therefore, the determination distance is larger than the restriction release threshold value.

Further, the restriction release threshold value may be a fixed value or a variable value. In a case in which restriction start threshold value is a variable value, control unit 15 may adjust the restriction release threshold value through a method similar to the method using the restriction start threshold value. Further, a magnitude relation between the restriction start threshold value and the restriction release threshold value is not particularly limited. For example, the restriction release threshold value may be larger than the restriction start threshold value. Further, the restriction release threshold value may be less than the restriction start threshold value. However, in the latter case, it is necessary to separately decide a process in a case in which the determination distance is less than the restriction start threshold value and larger than the restriction release threshold value. For example, in a case in which the determination distance varies from a value smaller than the restriction release threshold value to a value larger than the restriction release threshold value, the control unit 15 may determine that the restriction release condition is satisfied.

Further, the restriction release threshold value may be prepared in two stages. In other words, the control unit 15 may prepare a first restriction release threshold value smaller than the restriction start threshold value and a second restriction release threshold value larger than the restriction start threshold value. Then, after the determination distance becomes less than the first restriction release threshold value, the control unit 15 compares the determination distance with the first restriction release threshold value. Then, in a case in which the determination distance becomes larger than the first restriction release threshold value, the control unit 15 may determine that the restriction release condition is satisfied. Further, after the determination distance becomes less than the second restriction release threshold value, the control unit 15 compares the determination distance with the second restriction release threshold value. Then, in a case in which the determination distance becomes larger than the second restriction release threshold value, the control unit 15 may determine that the restriction release condition is satisfied. By setting the restriction release threshold value to be smaller than the restriction start threshold value, the control unit 15 can release the restriction of the movement of the indication position in a shorter time. Accordingly, the user can perform the selection manipulation with less uncomfortable feeling. Further, the restriction release threshold value may be the same value as the restriction start threshold value, but in this case, for example, the restriction state and the restriction release state are likely to change (frequently) due to movement (shaking) of the hand unintended by the user. Therefore, it is preferable that the restriction release threshold value and the restriction start threshold value be different values.

In step S80, the control unit 15 releases the fixing of the indication position. In other words, the control unit 15 releases the restriction of the movement of the indication position. After the restriction of the movement of the indication position is released, control unit 15 moves the indication position in accordance with the pointing manipulation of the user. Therefore, while the movement of the indication position is being restricted, the control unit 15 releases the restriction on the basis of the determination that the distance between the first manipulator and the second manipulator is determined to be larger than a second distance. The second distance is a distance corresponding to the restriction release threshold value. Further, the second distance may be larger than the first distance.

In step S90, the control unit 15 determines whether or not the action start condition is satisfied. Specifically, the control unit 15 determines whether or not the above-described determination distance is less than the action start (Thr for starting an action) threshold value. In a case in which the determination distance is determined to be less than the action start threshold value, the control unit 15 causes the process to proceed to step S90. In a case in which the determination distance is determined to be equal to or larger than the action start threshold value, the control unit 15 causes the process to proceed to step S110. In a case in which the user performs the pinch-in manipulation, the interval between the fingertips decreases. In other words, the determination distance decreases. Therefore, if the user performs the pinch-in manipulation, the determination distance becomes less than the action start threshold value at a certain timing.

Figure 10:
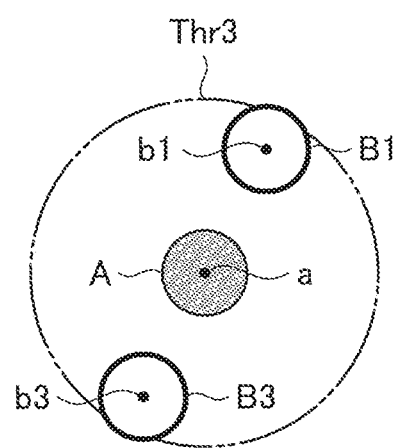
FIG. 10 is an explanatory diagram illustrating a display example performed by an information processing device.

FIG. 10 illustrates an example in which the determination distance is less than the action start threshold value. A frame Thr3 in FIG. 10 indicates the action start threshold value. In other words, a center point of frame Thr3 is the indication position a, and a radius is the action start threshold value. In FIG. 10, all of display positions b1 and b3 of fingertip images B1 and B3 are arranged inside the frame Thr3. Therefore, the determination distance is less than the action start threshold value.

Here, the action start threshold value may be a fixed value or a variable value. In a case in which the action start threshold value is a variable value, control unit 15 may adjust the restriction release threshold value by a method similar to the method using the restriction start threshold value. Further, the action start threshold value is a value smaller than the restriction start threshold value and the restriction release threshold value.

In step S100, the control unit 15 performs an action based on the indication position. Specifically, the control unit 15 selects an object placed on the indication position. Therefore, the control unit 15 performs an action based on the indication position in the display region on the basis of the determination that a distance between the first manipulator and the second manipulator is smaller than a third distance. Here, the third distance is a distance corresponding to the action start threshold value. Further, the first distance may be larger than the third distance. Thereafter, the control unit 15 causes the process to proceed to step S110.

In step S110, the control unit 15 decides a method of displaying the cursor and the fingertip image. For example, the control unit 15 decides the shapes or the like of the cursor and the fingertip image. For example, the cursor and the fingertip image may be circular image illustrated in FIG. 4. Further, the fingertip image may not be displayed.

In step S120, the control unit 15 generates the display control information related to the indication position, the display position of the fingertip image, the display method decided in step S110, the object decided in step S100, and the like. Then, the control unit 15 outputs the display control information to the display control unit 13. The display control unit 13 controls the display unit 14 on the basis of the display control information. The display unit 14 displays various kinds of images under the control of the display control unit 13. Specifically, the display unit 14 displays various kinds of objects in the display region X, displays the cursor at the indication position in the display region X, and displays the fingertip image at the display position of the fingertip image. Further, in a case in which a certain object is selected in step S100, for example, the display unit 14 displays an object corresponding to the selected object.

As described above, according to the present embodiment, the information processing device 10 restricts the movement of the indication position responsive to the pointing manipulation, and thus it is possible to improve the manipulability in a case in which an input manipulation is performed using a plurality of fingertips. Specifically, the information processing device 10 fixes the indication position in a case in which the user performs the pinch-in manipulation. Therefore, since the information processing device 10 can suppress the shift of the indication position, an object unintended by the user is unlikely to be selected.

Further, since the information processing device 10 decides the indication position on the basis of the positions of a plurality of fingertips, the user can easily move the indication position to a desired position. Further, since the control unit 15 restricts the movement of the indication position in a case in which a predetermined restriction start condition is satisfied, the user can stably indicate a desired position. The restriction of the movement of the indication position can be performed more stably. Particularly, the information processing device 10 restricts the movement of the indication position by fixing the indication position. Therefore, the user can more reliably select a desired object.

Further, the information processing device 10 restricts the movement of the indication position in a case in which the determination distance is less than the restriction start threshold value. Here, the determination distance is reduced, for example, if the user performs the pinch-in manipulation. For this reason, the movement of the indication position is restricted while the user is performing the pinch-in manipulation. Therefore, the information processing device 10 can more reliably suppress the shift of the indication position during the pinch-in manipulation.

Further, the information processing device 10 releases the restriction of the movement of the indication position in a case in which the restriction release condition is satisfied. Therefore, the information processing device 10 can release the restriction of the movement of the indication position, for example, in a case in which the user does not desire to restrict the movement of the indication position.

Further, the information processing device 10 releases the restriction of the movement of the indication position in a case in which the determination distance is larger than the restriction release threshold value. Here, the determination distance is increased, for example, if the user performs the pinch-out manipulation. Therefore, in a case in which the user does not desire to restrict the movement of the indication position, the user can release the restriction by performing the pinch-out manipulation. Therefore, the user can release the restriction with a simple manipulation.

Further, the information processing device 10 performs the action based on the indication position in a case in which the action start condition is satisfied. Specifically, the information processing device 10 selects an object on the indication position. Accordingly, the user can select a desired object by causing the indication position to be superimposed on a desired object and performing a manipulation satisfying the action start condition.

Further, the information processing device 10 restricts the movement of the indication position in a case in which the determination distance is less than the restriction start threshold value. Here, the determination distance is reduced, for example, if the user performs the pinch-in manipulation. Therefore, the user can select a desired object by performing the pinch-in manipulation. Further, since the movement of the indication position is restricted during the pinch-in manipulation, the user can select a desired object with a high degree of certainty.

It will be appreciated that the above-described effects are merely explanatory or exemplary and are not limited. In other words, the technology according to the present disclosure may have other effects obvious to those skilled in the art from the description of this specification in addition to or in place of the above-described effects.

The configuration and the basic process of the information processing device 10 have been described above. Here, the present embodiment is not limited to the above-described example, and various modified examples are applicable. In this regard, various kinds of modified examples will be described below. Further, processes other than processes described in the following modified examples are performed in accordance with the basic process described above. Further, in a case in which the processes described in the following modified examples and the basic process overlap, the processes may be performed in parallel within a range in which there is no inconsistency, or either of them may be selectively performed.

4. First Modified Example

A first modified example relates to a manipulator. In the above-described embodiment, a plurality of manipulators are the fingertips of the user. However, the manipulator is not limited to the fingertip of the user. For example, a plurality of manipulators may be, for example, all the arms of the user, the upper and lower eyelids, certain stick-like objects (for example, pens or the like), and the like. In a case in which all the arms of the user are manipulators, the user performs the pointing manipulation, the pinch-in manipulation, and the pinch-out manipulation using two arms. For example, the user performs the pointing manipulation by moving the two arms in parallel. Further, the user performs the pinch-in manipulation by narrowing an interval between the arms and performs the pinch-out manipulation by widening the interval between the arms. For example, the control unit 15 sets a crossing point of an extension line in the length direction of the arm and the display region X as a display position of the arm.

In a case in which the eyelids of the user are manipulation values, the user performs the pointing manipulation, the pinch-in manipulation, and the pinch-out manipulation using the eyelids. For example, the user performs the pointing manipulation by moving the upper and lower eyelids in parallel (actually, moving the head). Further, the user performs the pinch-in manipulation by closing the eyelids and performs the pinch-out manipulation by opening the eyelids. For example, the control unit 15 sets a crossing point of a vertical line drawn from the center of the eyelid to the display region X and the display region X as the display position of the eyelid.

In a case in which the stick-like object is a manipulator, the user performs the pointing manipulation, the pinch-in manipulation, and the pinch-out manipulation using a plurality of stick-like objects. For example, the user performs the pointing manipulation by moving a plurality of stick-like objects in parallel. Further, the user performs the pinch-in manipulation by narrowing an interval between the stick-like objects and performs the pinch-out manipulation by widening the interval between the stick-like objects. For example, the control unit 15 sets a crossing point of an extension line in the length direction of the stick-like object and the display region X as the display position of the stick-like object.

Further, in the above-described embodiment, the pointing manipulation, the pinch-in manipulation, and the pinch-out manipulation are performed using the same manipulator (here, the fingertip), but the pointing manipulation may be performed using a manipulator different from fingertip. For example, the pointing manipulation may be performed with the arm of the user. In this case, the user performs the pointing manipulation by moving the arm, and performs the object selection manipulation by performing the pinch-in manipulation. For example, the control unit 15 may set a crossing point of an extension line in the length direction of the arm and the display region X as the indication position. Further, the pointing manipulation may be performed using the line of sight of the user. The line of sight of the user can be specified on the basis of the detection information. In this case, the user performs the pointing manipulation by moving the line of sight and performs the object selection manipulation by performing the pinch-in manipulation. For example, the control unit 15 may set a crossing point of the line of sight and the display region X as the indication position. Further, the pointing manipulation may be performed using the palm of the user. In this case, in this case, the user performs the pointing manipulation by moving the palm (actually, moving the arm) and performs the object selection manipulation by performing the pinch-in manipulation. For example, the control unit 15 may set a crossing point of a perpendicular line drawn from a center point of the palm to the display region X and the display region X as the indication position.

5. Second Modified Example

A second modified example is a modified example related to an external configuration of the information processing device 10. As illustrated in FIG. 1, in the above-described embodiment, the information processing device 10 is a stationary type device as illustrated in FIG. 1. However, the information processing device 10 is not limited to a stationary device. In other words, the information processing device 10 may be any device as long as an input manipulation using a plurality of fingertips can be received.

For example, the information processing device 10 may be a display device capable of receiving a touch manipulation performed by a plurality of fingertips. In the display device, a touch panel is mounted on a display surface of a display (in this example, the display surface is the display region X), and the touch panel can receive the touch manipulation performed by a plurality of fingertips.

Further, the information processing device 10 may be a device that can be worn on the user, a so-called wearable device. More specifically, the information processing device 10 may be a transmissive head mounted display. The transmissive head mounted display may be a goggle type, an eyeglasses type, or another type. In this case, for example, the control unit 15 may set a crossing point of an extension line in the length direction of the finger and a real object in a real space or an AR image (corresponding to the above-described object) as the display position of the fingertip. Further, the information processing device 10 may be a so-called head-up display.

6. Third Modified Example

Figure 11:
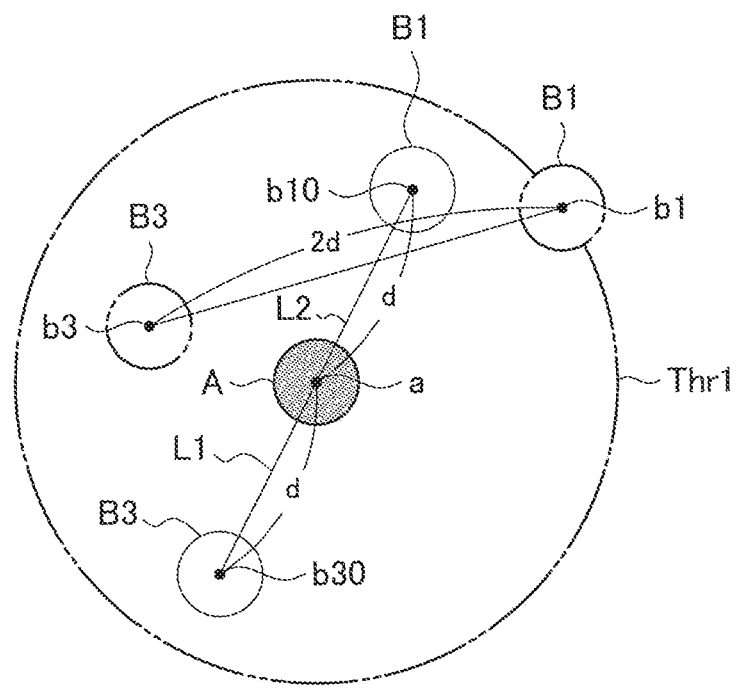
FIG. 11 is an explanatory diagram illustrating a display example performed by an information processing device.

A third modified example is a modified example related to the display position of the fingertip. The third modified example will be described below with reference to FIGS. 3, 11, and 12. In the above-described embodiment, the control unit 15 specifies the display position of the fingertip on the basis of the position of the fingertip. However, in this process, the display position moves arbitrarily in accordance with the position of the fingertip of the user, and thus the user may be confused by the pinch-in manipulation and the pinch-out manipulation. Therefore, in the third modified example, after the indication position is fixed, the trajectory of the display position is restricted. Specifically, the control unit 15 performs the following processing in step S30 after fixing the indication position. In other words, the control unit 15 specifies a tentative display position of the fingertip in the display region X on the basis of the position of the fingertip. The tentative display position corresponds to the display position in the above-described embodiment. In other words, the tentative display position indicates an indication position at which the restriction of the movement of the display position is not performed. Tentative display positions b1 and b3 illustrated in FIG. 11 are examples of the tentative display position. Further, in this example, the user performs the pinch-in manipulation using the index finger and the thumb. The tentative display position b1 corresponds to the index finger, and the tentative display position b3 corresponds to the thumb. In the above-described embodiment, the fingertip images B1 and B3 are displayed at the tentative display positions b1 and b3.

Then, the control unit 15 calculates a distance between the tentative display positions. For example, the control unit 15 calculates the distance (=2d) between the tentative display positions b1 and b3. Then, the control unit 15 draws a first trajectory line segment extending outward from the indication position. For example, the control unit 15 draws a first trajectory line segment L1 extending outward from the indication position a. A direction of the first trajectory line segment is not particularly limited and may be arbitrarily set by the user or may be preset. Further, a line segment connecting the display position and the indication position in a case in which the restriction start condition is satisfied may be used as the trajectory line segment. Then, the control unit 15 extracts a point at which the distance from the indication position is a half of the distance between the tentative display positions from the first trajectory line segment. The control unit 15 sets this point as the display position of the fingertip. For example, the control unit 15 extracts a point in which the distance from the indication position a is d from the first trajectory line segment L1. The control unit 15 sets this point as a display position b30 of the fingertip image B3.

Figure 12:
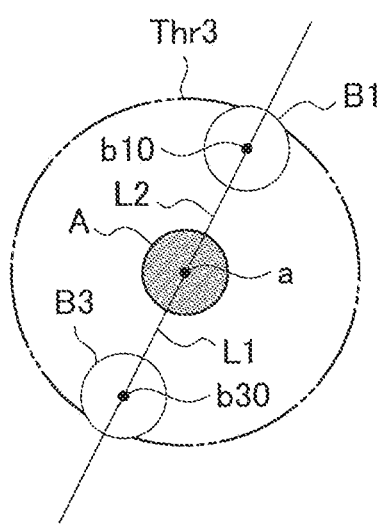
FIG. 12 is an explanatory diagram illustrating a display example performed by an information processing device.

Then, control unit 15 draws a second trajectory straight line extending from the indication position in a direction opposite to the first trajectory straight line. For example, the control unit 15 draws a second trajectory line segment L2 extending from the indication position a in the opposite direction to the first trajectory straight line L1. Then, the control unit 15 extracts a point at which the distance from the indication position is a half of the distance between the tentative display positions from the second trajectory line segment. The control unit 15 sets this point as the display position of the fingertip. For example, the control unit 15 extracts a point in which the distance from the indication position a is d from the second trajectory line segment L2. The control unit 15 sets this point as a display position b10 of the fingertip image B1. Therefore, in the third modified example, the fingertip image moves on the first trajectory line segment and the second trajectory line segment regardless of the actual display position of the fingertip (that is, the tentative display position). In other words, the trajectory of the display position is restricted. As illustrated in FIG. 12, the control unit 13 may cause the fingertip image to move on the first trajectory line segment and the second trajectory line segment until the action start condition is satisfied. Accordingly, the user can perform the pinch-in manipulation and the pinch-out manipulation more stably. Further, in the example of FIG. 11, the decision order of the tentative display positions b10 and b30 may be opposite to the above example.

Further, the example in which the user performs the pinch-in manipulation with the two fingers has been described above, but a similar process can be performed even in a case in which the user performs the pinch-in manipulation with three or more fingers. For example, in a case in which the user performs the pinch-in manipulation with three fingers, the trajectory line segment includes, for example, three line segments extending from the indication position. An angle between the trajectory line segments may be, for example, 120°. In other words, the control unit 15 draws as many trajectory line segments as fingers of performing the pinch-in manipulation and set the angles between these trajectory line segments to be the same angle. For example, in a case in which the number of trajectory line segments is two, the angle between the trajectory line segments is set to 180°, and in a case in which the number of trajectory line segments is three, the angle between the trajectory line segments is set to 120°. Further, in a case in which the number of trajectory line segments is four, the angle between the trajectory line segments is set to 90°, and in a case in which the number of trajectory line segments is five, the angle between the trajectory line segments is set to 72°. It will be appreciated that the trajectory line segment pattern is not limited to this example.

7. Fourth Modified Example

In the above-described embodiment, the restriction start condition is a condition that the determination distance is less than the restriction start threshold value. However, the restriction start condition is not limited to this example. A fourth modified example is a modified example related to the restriction start condition. In the fourth modified example, the restriction start condition is a condition that the speed of the pinch-in manipulation is equal to or higher than a predetermined speed. In other words, in a case in which the user performs the pinch-in manipulation fast, the control unit 15 fixes the indication position regardless of the determination distance. This is because the user is likely to select the object on the indication position in a case in which the user performs the pinch-in manipulation fast. Further, instead of using the determination distance, coordinates of the display position may be used. In other words, the control unit 15 sets a determination region centered on the indication position (the determination region is, for example, a region inside the frame Thr1 illustrated in FIG. 6). Then, the control unit 15 may determine that the restriction start condition is satisfied in a case in which the coordinates of the display position are included in the determination region. A similar condition can be applied to the restriction release condition and the action start condition. The control unit 15 may use both the condition of the basic process and the condition of the fourth modified example as the restriction start condition, the restriction release condition, and the action start condition, or one of the conditions may be selectively used.

8. Fifth Modified Example

In the above-described embodiment, the movement of the indication position is restricted by fixing the indication position. However, the method of restricting the movement of the indication position is not limited to this method. A fifth modified example is a modified example related to the method of restricting the movement of the indication position. The fifth modified example will be described below with reference to FIG. 13.

In other words, in a case in which the restriction start condition is satisfied, the control unit 15 determines whether or not there is an object on the indication position. Then, in a case in which there is an object on the indication position, the control unit 15 erases the cursor and highlights the object. In other words, the control unit 15 fixes the indication position to the object and causes the cursor to be absorbed into the object. Here, the causing of the cursor to be absorbed into the object means, for example, erasing the cursor and highlighting the object. Here, the control unit 15 may display an animation in which the cursor is absorbed (for example, attracted) into the object when the cursor is absorbed into the object. The control unit 15 may also erase the fingertip image. The fingertip image and the cursor may be displayed without change. Accordingly, the object on the indication position is focused. For example, in a case in which there is an object 50 illustrated in FIG. 13 on the indication position, the control unit 15 highlights the object

Figure 13:
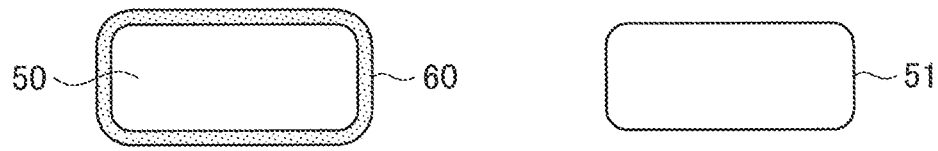
FIG. 13 is an explanatory diagram illustrating a display example performed by an information processing device.

50. A method of highlighting object is not particularly limited, and it is not particularly restricted if it is a method of displaying the object in a display form different from other objects. For example, the control unit 15 may cause a frame image surrounding an object to be displayed superimposed on the object. In the example of FIG. 13, the control unit 15 may cause a frame image 60 to be displayed superimposed on the object 50. According to the fifth modified example, the user can easily understand an indicated object. The control unit 15 selects the highlighted object in a case in which the action start condition is satisfied. Further, the control unit 15 may highlight the object even in a case in which the non-restricted indication position is superimposed on the object.

9. Sixth Modified Example

A sixth modified example is a modified example related to a process after the process of the fifth modified example is performed. The sixth modified example will be described with reference to FIGS. 13 and 14.

The control unit 15 performs the following processing after the process according to the fifth modified example is performed. In other words, the control unit 15 specifies the display position of the fingertip on the basis of the position of the fingertip. Then, the control unit 15 specifies the tentative indication position on the basis of the display position of the fingertip. Here, the tentative indication position has a role as a provisional indication position. In other words, in the fifth modified example, once the indication position is fixed to an object, the indication position is fixed even in a case in which the display position of the fingertip image changes. In this regard, in the sixth modified example, the tentative indication position is specified separately from the indication position, and the tentative indication position is moved on the basis of the display position of the fingertip image. The tentative indication position is, for example, the center of gravity position of the display position. In other words, a method of calculating the tentative display position may be similar to the method of calculating the display position. Then, the control unit 15 determines whether or not the tentative display position is moved onto another object. In a case in which the tentative display position is determined to be on another object, the control unit 15 sets the tentative display position as a new indication position while maintaining the restriction of the movement of the display position. In other words, the control unit 15 fixes the display position to another object and highlights another object. In other words, the focus is moved to another object. Further, in this case, the cursor may be displayed at the tentative indication position.

Figure 14:
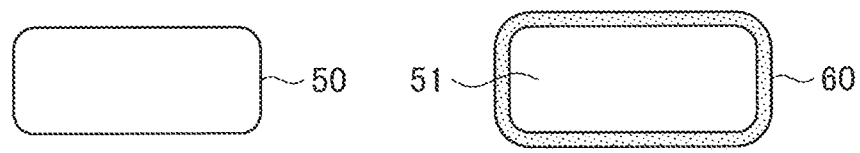
FIG. 14 is an explanatory diagram illustrating a display example performed by an information processing device.

For example, as illustrated in FIG. 14, in a case in which the tentative display position is moved to an object 51, the control unit 15 highlights the object 51. Therefore, for example, the user causes the object 50 to be highlighted and then moves the hand to the object 51 side while maintaining the interval between the fingertips (that is, the shape of the hand). Accordingly, the focus is moved to the object 51. Accordingly, the user can easily select a desired object. Further, in a case in which the restriction release condition is satisfied before the focus is moved to the object 51, the control unit 15 cancels the highlight display of the object 50. Further, the control unit 15 selects the object 50 in a case in which the action start condition is satisfied before the focus is moved to the object 51.

10. Seventh Modified Example

A seventh modified example is a modified example similar to the fifth modified example. The seventh modified example will be described below with reference to FIGS. 15 and 16.

Figure 15:
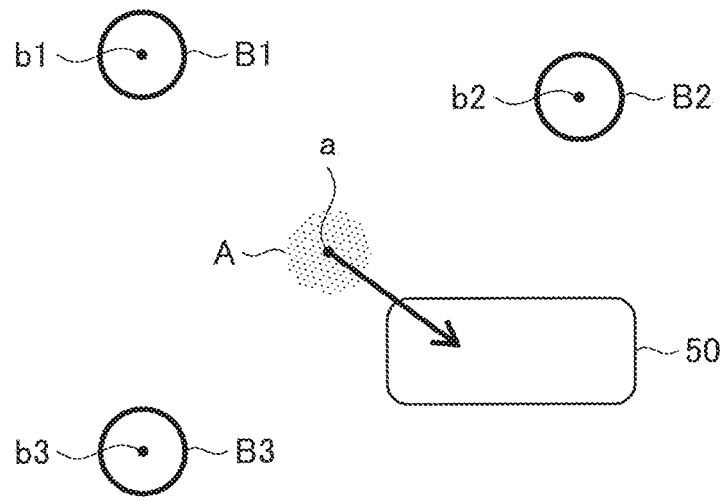
FIG. 15 is an explanatory diagram illustrating a display example performed by an information processing device.
Figure 16:
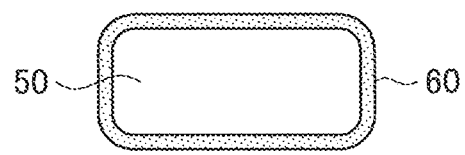
FIG. 16 is an explanatory diagram illustrating a display example performed by an information processing device.

In other words, in a case in which the restriction start condition is satisfied, the control unit 15 determines whether or not the indication position is within a predetermined absorption range from the object. The size of the absorption range is not particularly limited and may be arbitrarily set by the user or may be set in advance. Further, in a case in which the indication position is determined to be within the absorption range from the object, the control unit 15 erases the cursor and highlights the object. In other words, the control unit 15 fixes the indication position to the object and cause the cursor to be absorbed into the object. The control unit 15 may also erase the fingertip image. The fingertip image and the cursor may be displayed without change. Accordingly, the object is focused. For example, in a case in which the indication position a is within a predetermined absorption range from the object 50 as illustrated in FIG. 15, the control unit 15 highlights the object 50 as illustrated in FIG. 16. Specifically, the control unit 15 causes the frame image 60 to be superimposed on the object 50. Further, the control unit 15 causes the cursor A to be absorbed into the object 50 and fixes the indication position a to the object 50. Further, the control unit 15 erases the fingertip images B1 to B3. According to the seventh modified example, the user can easily understand an indicated object. Further, the user can fix the indication position to a desired object by simply bringing the indication position closer to the desired object. Therefore, the user can easily fix the indication position to the desired object.

11. Eighth Modified Example

Figure 17:
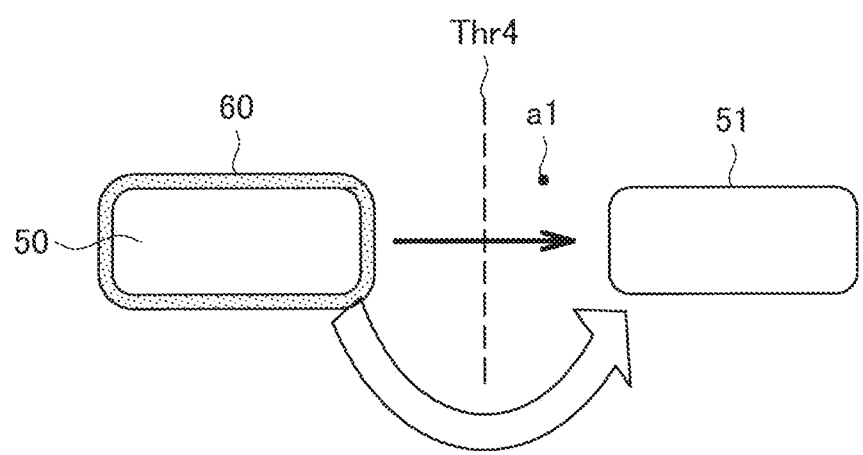
FIG. 17 is an explanatory diagram illustrating a display example performed by an information processing device.

An eighth modified example is a modified example similar to the sixth modified example. The eighth modified example will be described below with reference to FIGS. 16 and 17. The control unit 15 performs the following processing after the process according to the seventh modified example is performed. In other words, the control unit 15 specifies the display position of the fingertip on the basis of the position of the fingertip. Then, the control unit 15 specifies the tentative indication position on the basis of the display position of the fingertip. The tentative indication position is similar to that of the sixth modified example. Then, the control unit 15 determines whether or not the tentative display position is within a predetermined absorption range from another object. The absorption range is similar to that of the seventh modified example. In a case in which the tentative display position is determined to be within a predetermined absorption range from another object, the control unit 15 fixes the display position to another object and highlights another object. In other words, the control unit 15 moves the indication position to the inside of another object and highlights another object while maintaining the restriction of the movement of the indication position. Accordingly, the control unit 15 moves the focus to another object. For example, in a case in which a tentative display position a1 is within a predetermined absorption range from the object 51 as illustrated in FIG. 17, the control unit 15 highlights the object 51 as illustrated in FIG. 14. A straight line Thr 4 indicates the absorption range for the object 51. In other words, a region on the right side of the straight line Thr 4 is the absorption range for the object 51. The straight line Thr 4 is not displayed but may be displayed.

Therefore, for example, the user causes the object 50 to be highlighted and then moves the hand to the object 51 side while maintaining the interval between the fingertips (that is, the shape of the hand). Accordingly, the focus is moved to the object 51. Accordingly, the user can easily select a desired object. Further, in a case in which the restriction release condition is satisfied before the focus is moved to the object 51, the control unit 15 cancels the highlight display of the object 50. Further, the control unit 15 selects the object 50 in a case in which the action start condition is satisfied before the focus is moved to the object 51.

12. Ninth Modified Example

In the above-described embodiment, the restriction release condition is a condition that the determination distance is larger than the restriction release threshold value. However, the restriction release condition is not limited to this example. The ninth modified example is a modified example related to the restriction release condition.

In the ninth modified example, the control unit 15 specifies the display position of the fingertip on the basis of the position of the fingertip. Then, the control unit 15 specifies the tentative indication position on the basis of the display position of the fingertip. The tentative indication position is similar to that of the sixth modified example. Then, the control unit 15 calculates a movement amount of the tentative indication position. Here, it is desirable to set the movement amount of the tentative indication position to, for example, a straight line distance from the tentative indication position at which the restriction of the movement of the indication position starts to the current tentative indication position. The control unit 15 determines whether or not the movement amount of the tentative indication position is larger than a predetermined restriction release movement amount. The magnitude of the restriction release movement amount is not particularly limited and may be arbitrarily set by the user or may be set in advance. Further, the restriction release movement amount may be adjusted in accordance with the state (the size or the density) of the object placed in the movement direction of the tentative indication position or the like. For example, in a case in which there are a plurality of objects in the movement direction of the tentative indication position, the user is likely to select one of the objects, and thus it may be desirable to release the restriction of the movement of the object at an early stage. Therefore, the restriction release movement amount may be small. Further, the restriction release movement amount may differ for each movement direction of the tentative indication position. Further, the restriction release movement amount may be adjusted in accordance with the moving speed of the tentative indication position. For example, the restriction release movement amount may decrease as the moving speed of the tentative indication position increases. It is because the user is estimated to be more likely to select other objects as the moving speed of the tentative indication position increase. Further, the restriction release movement amount may be adjusted in accordance with the size of the hand of the user, an arrangement of objects, or the like.

Further, in a case in which the movement amount of the tentative indication position is determined to be larger than a predetermined restriction release movement amount, the control unit 15 releases the restriction of the movement of the indication position. Therefore, for example, the user moves the hand in a direction away from the indication position while maintaining the interval between the fingertips (that is, the shape of the hand) after the movement of the indication position is restricted. Accordingly, the user can release the restriction of movement of the indication position.

In the ninth modified example, in a case in which the restriction of the movement of the indication position is released, the tentative display position becomes a new display position. In this case, the control unit 15 may instantaneously move the cursor from the restricted indication position to the new display position or may continuously move the cursor to the new the indication position. In other words, the control unit 15 may perform control such that an animation in which the cursor is moved to the new the indication position is displayed. In the latter case, the control unit 15 can express the movement of the cursor more naturally. A similar process may also be performed in a tenth modified example to be described later.

Further, in the ninth modified example, even after the restriction of the movement of the indication position is released, the determination distance may be less than the restriction start threshold value. In this regard, the control unit 15 may reduce the restriction start threshold value after releasing the restriction of the movement of the indication position in the ninth modified example. The same applies to the tenth modified example to be described later.

13. Tenth Modified Example

The tenth modified example is a modified example similar to the ninth modified example. In the tenth modified example, the control unit 15 specifies the tentative indication position as in the ninth modified example. Then, the control unit 15 calculates the moving speed of the tentative indication position. Here, the moving speed of the tentative indication position is calculated, for example, by the following process. In other words, the control unit 15 measures a distance from the tentative indication position specified with a previous processing cycle (the processing cycle in FIG. 3) to the tentative indication position specified with a current processing cycle. Then, the control unit 15 divides the distance by a period of the processing cycle. Accordingly, the control unit 15 calculates the moving speed of the tentative indication position. The control unit 15 determines whether or not the moving speed of the tentative indication position is larger than a predetermined restriction release speed. The magnitude of the restriction release speed is not particularly limited and may be arbitrarily set by the user or may be set in advance. The restriction release speed may be adjusted by a method similar to the method using the restriction release movement amount. Further, in a case in which the moving speed of the tentative indication position is determined to be larger than a predetermined restriction release speed, the control unit 15 releases the restriction of the movement of the indication position. Therefore, for example, the user quickly moves the hand in a direction away from the indication position while maintaining the interval between the fingertips (that is, the shape of the hand) after the movement of the indication position is restricted. Accordingly, the user can release the restriction of movement of the indication position.

14. Eleventh Modified Example

Figure 18:
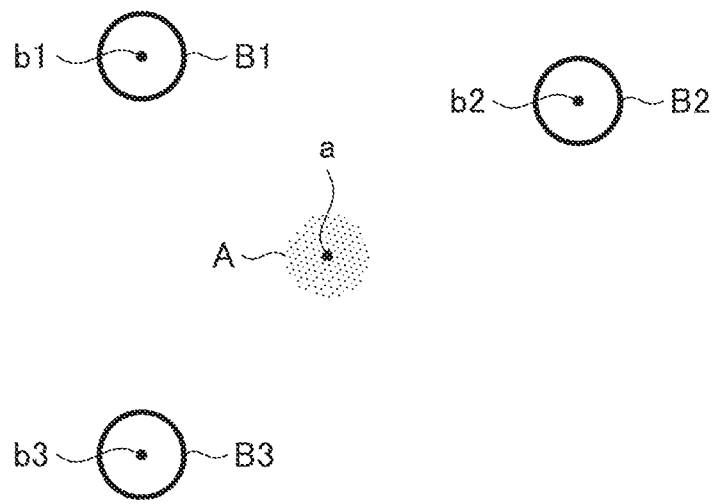
FIG. 18 is an explanatory diagram illustrating a display example performed by an information processing device.
Figure 19:
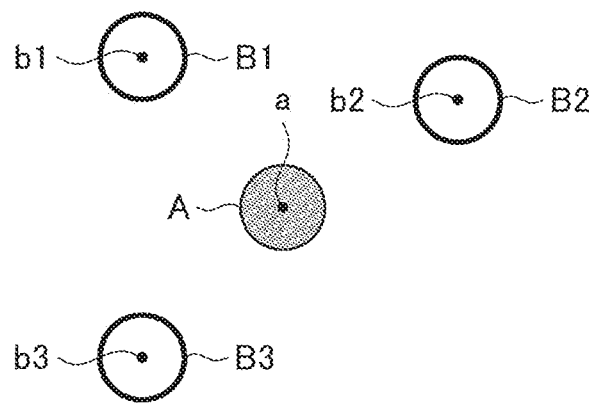
FIG. 19 is an explanatory diagram illustrating a display example performed by an information processing device.
Figure 20:
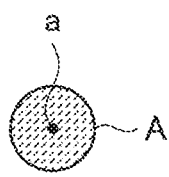
FIG. 20 is an explanatory diagram illustrating a display example performed by an information processing device.

Next, an eleventh modified example will be explained. In the eleventh modified example, the control unit 15 performs control such that a notification indicating that the movement of the indication position is restricted is given to the user who manipulates a plurality of manipulators in a case in which the movement of the indication position is restricted. More specifically, the control unit 15 changes the display form of the cursor in accordance with the state of the indication position. An example is illustrated in FIGS. 18 to 20. It will be appreciated that the example of FIGS. 18 to 20 is an example of the display form. In FIG. 18, the control unit 15 does not restrict the movement of the indication position a. In this case, the control unit 15 causes the color of the cursor A to be thinner. Further, the control unit 15 increases permeability of the cursor A. Further, the control unit 15 blurs an area around the cursor A. Further, the control unit 15 may selectively adjust one or more types of the color of the cursor A, the permeability of the cursor A, and the blur of the area around the cursor A.

In FIG. 19, the control unit 15 restricts the movement of the indication position a. In this case, the control unit 15 causes the color of the cursor A to be darker than in the example of FIG. 18. Further, the control unit 15 causes the permeability of the cursor A to be lower than in the example of FIG. 18. Further, the control unit 15 causes the blur of the area around the cursor A to be smaller than in the example in FIG. 18. Further, the control unit 15 may selectively adjust one or more types of the color of the cursor A, the permeability of the cursor A, and the blur of the area around the cursor A.

In FIG. 20, the control unit 15 selects the object on the indication position a. In this case, the control unit 15 sets the color of the cursor A to a color different from those of FIGS. 18 and 19. Further, the control unit 15 may set the permeability of the cursor A and the blur amount of the area around the cursor A to values different from those of the examples of FIGS. 18 and 19. In the eleventh modified example, the user can easily understand the state of the indication position.

Further, in the above example, the control unit 15 changes the color of the cursor A, the permeability of the cursor A, and the blur of the area around the cursor A, but it will be appreciated that another display form may be adjusted. For example, the control unit 15 may adjust a shape, brightness, a size, or the like of the cursor A. Further, the control unit 15 may display the cursor A using an animation differing for each state of the indication position.

Further, in the above example, when the object is selected, the display form of the cursor is changed, but the display form of the selected object may be changed. For example, the control unit 15 may display an animation to restore the original after the selected object is reduced.

Further, in the eleventh modified example, a notification indicating the state change of the indication position is given to the user through a visual change, but it will be appreciated that a notification indicating the state change of the indication position may be given to the user by other methods. For example, the control unit 15 may give a notification indicating the state change of the indication position to the user using a sound, a vibration, or the like. In a case in which a notification indicating the state change of the indication position is given to the user using a sound, it is preferable that the information processing device 10 is equipped with a speaker or the like. A portable speaker capable of communicating with the information processing device 10 may be carried by the user. Further, in a case in which a notification indicating the state change of the indication position is given to the user using a vibration, a vibratable wearable device capable of communicating with the information processing device 10 may be carried by the user. The control unit 15 may perform the following process in addition to the above-described process (or in place of the above-described process). In other words, in a case in which the movement of the indication position is restricted, the control unit 15 may give a notification to the user through a process of outputting a sound indicating that the restriction of the movement of the indication position, a process of displaying a separate image from the cursor, or the like.

15. Twelfth Modified Example

Next, a twelfth modified example. In the twelfth modified example, the control unit 15 displays the cursor in a display form according to a distance between the first manipulator and the second manipulator. In other words, the control unit 15 changes the display form of the cursor in accordance with a degree of achievement of the restriction start condition and a degree of achievement of the action start condition. An example of the twelfth modified example will be described below with reference to FIGS. 21 and 22.

Figure 21:
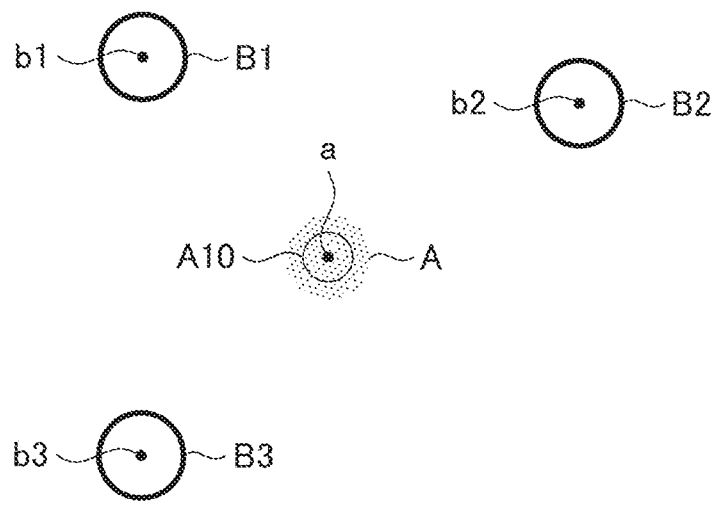
FIG. 21 is an explanatory diagram illustrating a display example performed by an information processing device.

In FIG. 21, the control unit 15 does not restrict the position of the indication position a. In this example, the control unit 15 displays a ring image A10 in the cursor A. Further, in this example, the control unit 15 displays the cursor A in a similar display form to that in the eleventh modified example. Then, the control unit 15 reduces the radius of the cursor A as a difference between the determination distance and the restriction start threshold value decreases (that is, as the degree of achievement increases). Then, when the determination distance becomes less than the restriction start threshold value, the control unit 15 reduces the radius of the cursor A to be smaller than the radius of the ring image A10. Therefore, in this example, the degree of achievement of the restriction start condition is indicated as a difference between the radius of the cursor A and the radius of the ring image A10.

Figure 22:
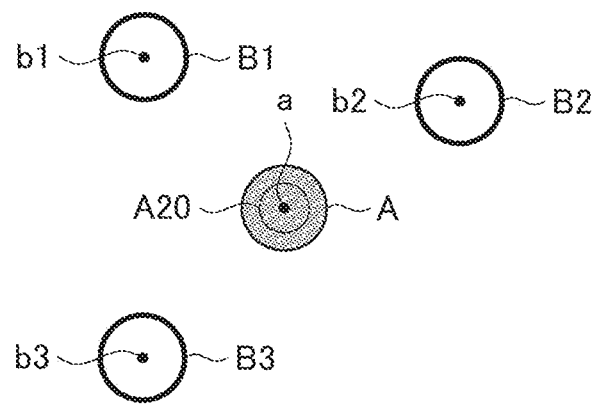
FIG. 22 is an explanatory diagram illustrating a display example performed by an information processing device.

In FIG. 22, the control unit 15 restricts the position of the indication position a. In this example, the control unit 15 displays a ring image A20 in the cursor A. Further, in this example, the control unit 15 displays the cursor A in a similar display form to that in the eleventh modified example. Then, the control unit 15 reduces the radius of the cursor A as the difference between the determination distance and the action start threshold value decreases (that is, as the degree of achievement increases). Then, when the determination distance becomes less than the action start threshold value, the control unit 15 reduces the radius of the cursor A to be smaller than the radius of the ring image A20. Therefore, in this example, the degree of achievement of the action start condition is indicated as a difference between the radius of the cursor A and the radius of ring image A20. Further, the degree of achievement of the action start condition may be indicated by the size of the object. For example, the control unit 15 may decrease the size of the object as the degree of achievement of the action start condition increases. Then, the control unit 15 may cause the action start condition to be satisfied in a case in which the object disappears. Further, the control unit 15 may change the color or the like of the object in accordance with the degree of achievement of the action start condition.

Further, although not illustrated here, it will be appreciated that a similar process can be applied to the restriction release condition. In this case, preferably, the control unit 15 causes a ring image larger than cursor A to be displayed around the cursor A in the example of FIG. 22. Then, the control unit 15 may increase the radius of the cursor A as the determination distance increases (that is, the degree of achievement increases). Then, when the determination distance becomes larger than restriction release threshold value, preferably, the control unit 15 increases the radius of the cursor A to be larger than the radius of the ring image.

Thus, in the twelfth modified example, the user can easily understand the degree of achievement of each condition. Further, it will be appreciated that the display form of the degree of achievement of each condition is not limited to the above examples. For example, the control unit 15 may darken the color of the cursor (or lower the permeability of the cursor) as the degree of achievement of the restriction start condition or the action start condition increases. Further, the control unit 15 may cause the color of the cursor to be thinner (or increase the permeability of the cursor) as the degree of achievement of the restriction release condition increases. It will be appreciated that a notification indicating the degree of achievement may be given to the user using a sound, a vibration, or the like as in the eleventh modified example.

16. Thirteenth Modified Example

Then, a thirteenth modified example will be described. The thirteenth modified example is a modified example related to the selection of the object. In other words, in the above-described embodiment, the control unit 15 selects the object on the indication position in a case in which the action start condition is satisfied. However, there are cases in which an object serving as a selection target (that is, an action target) is not placed at the indication position. Examples of the case include a case in which there is no object on the indication position and a case in which there is an object on the indication position, but the object is unable to be selected. In this regard, in the thirteenth modified example, the control unit 15 performs the following process.

In a case in which the restriction start condition is satisfied, the control unit 15 determines whether or not there is an object serving as a selection target on the indication position. Here, the object serving as the selection target is an object on which the user is able to perform the selection manipulation. Examples of the object include various kinds of buttons (including radio buttons), text boxes, seek bars, check boxes, draggable objects, and parts for turning over pages of electronic books or the like. It will be appreciated that the object on which the user is able to perform the selection manipulation is not limited to the above examples.

Further, in a case in which it is determined that there is an object serving as the selection target on the indication position, the control unit 15 fixes the indication position. In other words, the control unit 15 performs a similar process to the basic process. On the other hand, in a case in which it is determined that there is no object serving as the selection target on the indication position, the control unit 15 performs control such that information indicating that there is no object serving as the selection target on the indication position is displayed instead of fixing the indication position. For example, the control unit 15 displays an animation in which the cursor disappears. More specifically, the control unit 15 may cause the cursor to disappear after enlarging the cursor. Further, the control unit 15 may cause the color to be thinner while enlarging the cursor and then cause the cursor to disappear. Further, the control unit 15 may display the cursor in a form similar to smoke and then cause the cursor to disappear. It will be appreciated that the animation is not limited to the above examples. Therefore, the control unit 15 gives a notification indicating that there is no object serving as the selection target on the indication position to the user.

Further, similarly to the eleventh modified example, a notification indicating that there is no object serving as the selection target on the indication position may be given to the user using a sound, a vibration, or the like. Further, the control unit 15 may fix the indication position even in a case in which there is no object serving as the selection target on the indication position. In this case, the control unit 15 may perform the above-described processing after the action start condition is satisfied.

Further, the above-described basic process and the modified examples may be arbitrarily combined and used. For example, the information processing device 10 may be a wearable device, and a manipulator for performing the pointing manipulation or the like may be an eyelid or the like (a combination of the first modified example and the second modified example).

Further, the control unit 15 may fix the indication position within the object while fixing the trajectory of the fingertip image (a combination of the third modified example and the fifth modified example). Further, in a case in which the indication position is presented on object or within a predetermined absorption range from object, the indication position may be fixed within the object (a combination of the fifth to eighth modified examples).

Further, in a case in which the movement amount of the tentative indication position is larger than a predetermined restriction release movement amount or the determination distance is larger than a predetermined restriction release threshold value, the control unit 15 may release the restriction of the movement of the indication position (a combination of the basic process and the ninth modified example).

Further, in a case in which the moving speed of the tentative indication position is larger than a predetermined restriction release speed or the determination distance is larger than a predetermined restriction release threshold value, the control unit 15 may release the restriction of the movement of the indication position (a combination of the basic process and the tenth modified example).

Further, in a case in which the speed of the pinch-in manipulation becomes equal to or higher than a predetermined speed or the determination distance becomes less than the restriction start threshold value, the control unit 15 may restrict the movement of the indication position (a combination of the basic process and the fourth modified example).

Further, the control unit 15 may change the display form of the indication position on the basis of the state of the indication position and the degree of achievement of each condition (a combination of the eleventh modified example and the twelfth modified example). For example, the control unit 15 may cause the frame image indicating the degree of achievement to be displayed in the cursor while changing the color or the like of the cursor in accordance with the state of the indication position.

Further, in a case in which the speed of the pinch-in manipulation becomes equal to or higher than a predetermined speed, the control unit 15 may determine whether or not there is an object serving as the selection target on the indication position. Then, in a case in which there is no object, the control unit 15 may control such that information indicating that there is no object is displayed (a combination of the fourth modified example and the thirteenth modified example).

17. Field of Application

A field of application of the information processing device 10 according to the present embodiment is not particularly limited, and the information processing device 10 according to the present embodiment may be applied to fields of automobiles, medical, and agriculture.

In a case in which the information processing device 10 is applied to automobiles, for example, the information processing device may be a head-up display. In this case, the display region X is specified on a front window of an automobile. An object displayed on the front window is preferably associated the automobile but may be, for example, an object for indicating driving content of the automobile. An example of such an object is an object for changing traction control (a button for selecting 4WD or 2WD or the like). An occupant of the automobile may select a desired object by performing the gesture manipulation (that is, the pointing manipulation, the pinch-in manipulation, and the pinch-out manipulation). Further, the information processing device 10 may be a car navigation device. In this case, an occupant of the automobile may select an object displayed on the information processing device 10 (for example, a destination in map information or the like) by performing the gesture manipulation.

In a case in which the information processing device 10 is applied to a medical field, the information processing device 10 may be installed in, for example, an operating room. In this case, the information processing device 10 displays objects related to surgery. An example of such an object is a viscera image of a patient observed with an endoscope or the like. For example, a surgeon selects a part serving as a treatment target from the objects displayed on the information processing device 10. The surgeon is unable to directly touch the information processing device 10 or the like during the treatment but can select a desired object through the gesture manipulation. Further, the size of the information processing device 10 is not particularly limited and may be a large size or a small size.

The information processing device 10 may be used as a control device of a medical robot that automatically performs surgery, dosing, and the like. In this case, the information processing device 10 displays, for example, an image or the like indicating a current external appearance of a patient (for example, an open abdominal state) as an object. Then, the surgeon selects, for example, a part serving as a treatment target from the object displayed on the information processing device 10. The medical robot performs desired treatment on the part selected by the surgeon.

In a case in which the information processing device 10 is applied to an agricultural field, information processing device 10 may be used, for example, for farm management. In other words, the information processing device 10 displays a video obtained by observing a farm from the sky as an object. Further, a farm manager selects a part of the farm. Thereafter, an employee of the farm or an automatic management device of the farm performs a desired procedure (for example, spraying of agricultural chemicals) or the like on the selected position.

It will be appreciated that the above examples are merely examples, and the information processing device 10 may be used for various fields and use applications.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An information processing device, including:

a control unit configured to decide an indication position for specifying a position in a display region on a basis of positions of a plurality of manipulators, in which the control unit restricts movement of the indication position responsive to movement of the manipulator on a basis of a state of the manipulator.

(2)

The information processing device according to (1), in which the control unit performs control such that a cursor is displayed in the display region on a basis of the indication position.

(3)

The information processing device according to (2), in which, in a case in which the movement of the indication position is restricted, the control unit performs control such that a notification indicating the restriction of the movement of the indication position is given to a user who manipulates the plurality of manipulators.

(4)

The information processing device according to (2) or (3), in which the control unit restricts the movement of the indication position on a basis of a determination that a distance between a first manipulator and a second manipulator included in the plurality of manipulators is smaller than a first distance.

(5)

The information processing device according to (4), in which the control unit performs control such that the cursor is displayed in a display form according to the distance between the first manipulator and the second manipulator.

(6)

The information processing device according to (4) or (5), in which the control unit performs control such that manipulator images are displayed at display positions of the plurality of manipulators, and performs control such that a manipulator image is displayed on a straight line passing through the cursor while the movement of the indication position is being restricted.

(7)

The information processing device according to any one of (4) to (6), in which, while the movement of the indication position is being restricted, the control unit releases the restriction on a basis of a determination that the distance between the first manipulator and the second manipulator is larger than a second distance.

(8)

The information processing device according to (7), in which the second distance is larger than the first distance.

(9)

The information processing device according to any one of (4) to (8), in which the control unit performs an action based on the indication position in the display region on a basis of a determination that the distance between the first manipulator and the second manipulator is smaller than a third distance.

(10)
The information processing device according to (9),
in which the first distance is larger than the third distance.

(11)
The information processing device according to (10),
in which the first manipulator is a thumb of a user, and
the second manipulator is an index finger or a middle finger of the same hand as the thumb.

(12)
The information processing device according to any one of (2) to (11),
in which, in a case in which the movement of the indication position is restricted, the control unit performs control such that the cursor is displayed in a display form different from a display form in a case in which the movement of the indication position is not restricted.

(13)
The information processing device according to any one of (2) to (12),
in which the control unit performs an action based on the indication position in the display region, and, in a case in which the movement of the indication position is restricted, the control unit performs control such that the cursor is displayed in a display form different from a display form in a case in which the action is performed.

(14)
The information processing device according to any one of (2) to (13),
in which, in a case in which the movement of the indication position present within a predetermined absorption range from an object in the display region is restricted, the control unit performs control such that the indication position is moved to an inside of the object and the object is displayed in a highlighted manner.

(15)
The information processing device according to any one of (2) to (14),
in which, in a case in which the movement of the indication position is restricted, the control unit specifies the indication position in a case in which the restriction is not performed as a tentative indication position, sets the tentative indication position as a new indication position after releasing the restriction, and performs control such that the cursor is continuously moved to the new indication position.

(16)
The information processing device according to (15),
in which, in a case in which the tentative indication position is within a predetermined absorption range from an object in the display region, the control unit moves the indication position to an inside of the object while maintaining the restriction of the movement of the indication position and, displays the object in a highlighted manner.

(17)
The information processing device according to any one of (2) to (16),
in which the control unit performs an action based on the indication position in the display region, and, in a case in which an object serving as a target of the action is not present at the indication position, the control unit gives a notification indicating that the object serving as the target of the action is not present at the indication position, to a user who manipulates the plurality of manipulators.

(18)
An information processing method, including:
deciding, by a control unit, an indication position for specifying a position in a display region on a basis of positions of a plurality of manipulators, and restricting movement of the indication position responsive to movement of the manipulator on a basis of a state of the manipulator.

(19)
A program causing a computer to execute:
a control function of deciding an indication position for specifying a position in a display region on a basis of positions of a plurality of manipulators,
in which the control function restricts movement of the indication position responsive to movement of the manipulator on a basis of a state of the manipulator.

REFERENCE SIGNS LIST 10 information processing device
11 detecting unit
12 manipulator operation recognizing unit
13 display control unit
14 display unit
15 control unit
A cursor
a indication position
a1 tentative indication position
B1 to B3 fingertip image
b1 to b3 display position
50, 51 object

The invention claimed is:

1. An information processing device, comprising:
a control unit configured to:
  determine an indication position to specify a position in a display region based on positions of a plurality of manipulators;
  restrict movement of the indication position responsive to movement of a manipulator of the plurality of manipulators based on a state of the manipulator; and
  control a display device to display a cursor in the display region based on the indication position, wherein the display device is controlled such that the cursor is displayed in a display form different from a display form in a case in which the movement of the indication position is not restricted.

2. The information processing device according to claim 1, wherein, in a case in which the movement of the indication position is restricted, the control unit is further configured to output a notification indicating the restriction of the movement of the indication position.

3. The information processing device according to claim 1, wherein the control unit is further configured to restrict the movement of the indication position based on a determination that a distance between a first manipulator and a second manipulator among the plurality of manipulators is smaller than a first distance.

4. The information processing device according to claim 3, wherein the control unit is further configured to control the display device such that the cursor is displayed in a display form according to the distance between the first manipulator and the second manipulator.

5. The information processing device according to claim 3, wherein the control unit is further configured to:
  control the display device such that manipulator images are displayed at display positions of the plurality of manipulators; and control the display device such that a manipulator image is displayed on a straight line passing through the cursor while the movement of the indication position is restricted.

6. The information processing device according to claim 3, wherein, while the movement of the indication position is restricted, the control unit is further configured to release the restriction based on a determination that the distance between the first manipulator and the second manipulator is larger than a second distance.

7. The information processing device according to claim 6, wherein the second distance is larger than the first distance.

8. The information processing device according to claim 3, wherein the control unit is further configured to execute an action based on the indication position in the display region and based on a determination that the distance between the first manipulator and the second manipulator is smaller than a third distance.

9. The information processing device according to claim 8, wherein the first distance is larger than the third distance.

10. The information processing device according to claim 9, wherein the first manipulator is a thumb of a hand, and the second manipulator is one of an index finger or a middle finger of the same hand as the thumb.

11. The information processing device according to claim 1, wherein the control unit is further configured to:
 execute an action based on the indication position in the display region; and
 in a case in which the movement of the indication position is restricted, control the display device such that the cursor is displayed in a display form different from a display form in a case in which the action is executed.

12. The information processing device according to claim 1, wherein, in a case in which the movement of the indication position present within a determined absorption range from an object in the display region is restricted, the control unit is further configured to control the display device such that the indication position is moved to an inside of the object and the object is displayed in a highlighted manner.

13. The information processing device according to claim 1, wherein, in a case in which the movement of the indication position is restricted, the control unit is further configured to:
 specify the indication position in a case in which the restriction is not applied as a tentative indication position;
 set the tentative indication position as a new indication position after releasing the restriction; and
 control the display device such that the cursor is continuously moved to the new indication position.

14. The information processing device according to claim 13, wherein, in a case in which the tentative indication position is within a determined absorption range from an object in the display region, the control unit is further configured to:
 move the indication position to an inside of the object while maintaining the restriction of the movement of the indication position; and
 display the object in a highlighted manner.

15. The information processing device according to claim 1, wherein the control unit is further configured to:
 execute an action based on the indication position in the display region; and
 in a case in which an object serving as a target of the action is not present at the indication position, output a notification indicating that the object serving as the target of the action is not present at the indication position.

16. An information processing method, comprising:
 determining, by a control unit, an indication position for specifying a position in a display region based on positions of a plurality of manipulators
 restricting, by the control unit, movement of the indication position responsive to movement of a manipulator of the plurality of manipulators based on a state of the manipulator; and
 controlling, by the control unit, a display device such that a cursor is displayed in the display region based on the indication position, wherein the display device is controlled such that the cursor is displayed in a display form different from a display form in a case in which the movement of the indication position is not restricted.

17. A non-transitory computer-readable medium having stored thereon, computer-executable instructions which, when executed by a computer, cause the computer to execute operations, the operations comprising:
 determining an indication position for specifying a position in a display region based on positions of a plurality of manipulators;
 restricting movement of the indication position responsive to movement of a manipulator of the plurality of manipulators based on a state of the manipulator; and
 controlling a display device such that a cursor is displayed in the display region based on the indication position, wherein the display device is controlled such that the cursor is displayed in a display form different from a display form in a case in which the movement of the indication position is not restricted.

18. An information processing device, comprising:
 a control unit configured to:
 determine an indication position to specify a position in a display region based on positions of a plurality of manipulators;
 restrict movement of the indication position responsive to movement of a manipulator of the plurality of manipulators based on a state of the manipulator;
 control a display device to display a cursor in the display region based on the indication position; and
 in a case in which the movement of the indication position is restricted, output a notification indicating the restriction of the movement of the indication position.

19. An information processing device, comprising:
 a control unit configured to:
 determine an indication position to specify a position in a display region based on positions of a plurality of manipulators;
 restrict movement of the indication position responsive to movement of a manipulator of the plurality of manipulators based on a state of the manipulator, wherein the movement of the indication position is restricted based on a determination that a distance between a first manipulator and a second manipulator among the plurality of manipulators is smaller than a specific distance; and
 control a display device to display a cursor in the display region based on the indication position.

* * * * *